(12) United States Patent
Davila et al.

(10) Patent No.: US 9,283,064 B2
(45) Date of Patent: Mar. 15, 2016

(54) METHODS AND SYSTEMS FOR TREATMENT OF PROLAPSE

(71) Applicant: AMS Research Corporation, Minnetonka, MN (US)

(72) Inventors: Guillermo H. Davila, Pompano Beach, FL (US); James E. Cox, Corcoran, MN (US); Kimberly A. Anderson, Eagan, MN (US)

(73) Assignee: AMS Research Corporation, Eden Prairie, MN (US)

( * ) Notice: Subject to any disclaimer, the term of this patent is extended or adjusted under 35 U.S.C. 154(b) by 0 days.

(21) Appl. No.: 14/743,259

(22) Filed: Jun. 18, 2015

(65) Prior Publication Data

US 2015/0282920 A1     Oct. 8, 2015

Related U.S. Application Data

(63) Continuation of application No. 14/025,988, filed on Sep. 13, 2013, now Pat. No. 9,060,839, which is a continuation of application No. 11/989,256, filed as application No. PCT/US2006/028828 on Jul. 25, 2006, now Pat. No. 8,535,217.

(60) Provisional application No. 60/702,705, filed on Jul. 26, 2005, provisional application No. 60/702,704, filed on Jul. 26, 2005, provisional application No. 60/702,700, filed on Jul. 26, 2005.

(51) Int. Cl.
*A61F 2/00* (2006.01)
*A61B 17/06* (2006.01)
*A61B 17/00* (2006.01)

(52) U.S. Cl.
CPC ......... *A61F 2/0063* (2013.01); *A61B 17/06109* (2013.01); *A61F 2/0045* (2013.01); *A61B 2017/00805* (2013.01); *A61B 2017/0608* (2013.01); *A61B 2017/06009* (2013.01); *A61B 2017/06042* (2013.01); *A61F 2002/0072* (2013.01)

(58) Field of Classification Search
CPC ....... A61F 2/00; A61F 2/0004; A61F 2/0045; A61F 2/0063; A61F 2002/0072; A61F 2/0031; A61F 2/0036; A61B 2017/00805; A61B 17/06061; A61B 2017/0445; A61B 2017/06009; A61B 2017/06042; A61B 2017/0608
See application file for complete search history.

(56) References Cited

U.S. PATENT DOCUMENTS 2,738,790 A   3/1956   Todt et al.
3,124,136 A   3/1964   Usher
(Continued)

FOREIGN PATENT DOCUMENTS

AU   2002241673   11/2005
CA     2404459    8/2005
(Continued)

OTHER PUBLICATIONS

"We're staying ahead of the curve" Introducing the IVS Tunneller Device for Tension Free Procedures, Tyco Healthcare, 3 pages (2002).

(Continued)

*Primary Examiner* — Charles A Marmor, II
*Assistant Examiner* — Carrie R Dorna
(74) *Attorney, Agent, or Firm* — Kagan Binder, PLLC

(57) ABSTRACT

Described are implants, tools, and related methods, for use in pelvic surgery to treat conditions such as prolapse, including embodiments of methods that involve a tissue path above the arcus tendineus.

19 Claims, 13 Drawing Sheets

(56) References Cited

U.S. PATENT DOCUMENTS

| | | | |
|---|---|---|---|
| 3,182,662 A | 5/1965 | Shirodkar |
| 3,311,110 A | 3/1967 | Singerman et al. |
| 3,384,073 A | 5/1968 | Van Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,815,576 A | 6/1974 | Balaban |
| 3,858,783 A | 1/1975 | Kapitanov et al. |
| 3,924,633 A | 12/1975 | Cook et al. |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,235,238 A | 11/1980 | Ogiu et al. |
| 4,246,660 A | 1/1981 | Wevers |
| 4,441,497 A | 4/1984 | Paudler |
| 4,509,516 A | 4/1985 | Richmond |
| 4,548,202 A | 10/1985 | Duncan |
| 4,632,100 A | 12/1986 | Somers et al. |
| 4,775,380 A | 10/1988 | Seedhom et al. |
| 4,857,041 A | 8/1989 | Annis et al. |
| 4,865,031 A | 9/1989 | O'Keeffe |
| 4,873,976 A | 10/1989 | Schreiber |
| 4,920,986 A | 5/1990 | Biswas |
| 4,932,962 A | 6/1990 | Yoon et al. |
| 4,938,760 A | 7/1990 | Burton et al. |
| 4,969,892 A | 11/1990 | Burton et al. |
| 5,007,894 A | 4/1991 | Enhorning |
| 5,012,822 A | 5/1991 | Schwarz |
| 5,013,292 A | 5/1991 | Lemay |
| 5,013,316 A | 5/1991 | Goble et al. |
| 5,019,032 A | 5/1991 | Robertson |
| 5,032,508 A | 7/1991 | Naughton et al. |
| 5,036,867 A | 8/1991 | Biswas |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,141,520 A | 8/1992 | Goble et al. |
| 5,149,329 A | 9/1992 | Richardson |
| 5,188,636 A | 2/1993 | Fedotov |
| 5,209,756 A | 5/1993 | Seedhom et al. |
| 5,250,033 A | 10/1993 | Evans et al. |
| 5,256,133 A | 10/1993 | Spitz |
| 5,269,783 A | 12/1993 | Sander |
| 5,281,237 A | 1/1994 | Gimpelson |
| 5,328,077 A | 7/1994 | Lou |
| 5,337,736 A | 8/1994 | Reddy |
| 5,362,294 A | 11/1994 | Seitzinger |
| 5,368,595 A | 11/1994 | Lewis |
| 5,370,650 A | 12/1994 | Tovey et al. |
| 5,370,662 A | 12/1994 | Stone et al. |
| 5,376,097 A | 12/1994 | Phillips |
| 5,383,904 A | 1/1995 | Totakura et al. |
| 5,386,836 A | 2/1995 | Biswas |
| 5,403,328 A | 4/1995 | Shallman |
| 5,413,598 A | 5/1995 | Moreland |
| 5,439,467 A | 8/1995 | Benderev et al. |
| 5,474,518 A | 12/1995 | Farrer Velazquez |
| 5,474,543 A | 12/1995 | McKay |
| 5,518,504 A | 5/1996 | Polyak |
| 5,520,700 A | 5/1996 | Beyar et al. |
| 5,520,703 A | 5/1996 | Essig |
| 5,527,342 A | 6/1996 | Pietrzak et al. |
| 5,544,664 A | 8/1996 | Benderev et al. |
| 5,562,689 A | 10/1996 | Green et al. |
| 5,571,139 A | 11/1996 | Jenkins, Jr. |
| 5,582,188 A | 12/1996 | Benderev et al. |
| 5,591,163 A | 1/1997 | Thompson |
| 5,591,206 A | 1/1997 | Moufarrege |
| 5,611,515 A | 3/1997 | Benderev et al. |
| 5,628,756 A | 5/1997 | Barker, Jr. et al. |
| 5,633,286 A | 5/1997 | Chen |
| 5,643,320 A | 7/1997 | Lower et al. |
| 5,669,935 A | 9/1997 | Rosenman et al. |
| 5,683,349 A | 11/1997 | Makower et al. |
| 5,697,931 A | 12/1997 | Thompson |
| 5,709,708 A | 1/1998 | Thal |
| 5,725,541 A | 3/1998 | Anspach, III et al. |
| 5,741,282 A | 4/1998 | Anspach, III et al. |
| 5,782,916 A | 7/1998 | Pintauro et al. |
| 5,785,640 A | 7/1998 | Kresch et al. |
| 5,807,403 A | 9/1998 | Beyar et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,860,425 A | 1/1999 | Benderev et al. |
| 5,899,909 A | 5/1999 | Claren et al. |
| 5,919,232 A | 7/1999 | Chaffringeon et al. |
| 5,922,026 A | 7/1999 | Chin |
| 5,925,047 A | 7/1999 | Errico et al. |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,972,000 A | 10/1999 | Beyar et al. |
| 5,980,558 A | 11/1999 | Wiley |
| 5,984,927 A | 11/1999 | Wenstrom, Jr. |
| 5,988,171 A | 11/1999 | Sohn et al. |
| 5,997,554 A | 12/1999 | Thompson |
| 6,010,447 A | 1/2000 | Kardjian |
| 6,027,523 A | 2/2000 | Schmieding |
| 6,030,393 A | 2/2000 | Corlew |
| 6,031,148 A | 2/2000 | Hayes et al. |
| 6,036,701 A | 3/2000 | Rosenman |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,099,538 A | 8/2000 | Moses |
| 6,099,551 A | 8/2000 | Gabbay |
| 6,099,552 A | 8/2000 | Adams |
| 6,106,545 A | 8/2000 | Egan |
| 6,110,101 A | 8/2000 | Tihon et al. |
| 6,117,067 A | 9/2000 | Gil-Vernet |
| 6,127,597 A | 10/2000 | Beyar et al. |
| 6,168,611 B1 | 1/2001 | Risvi |
| 6,200,330 B1 | 3/2001 | Benderev et al. |
| 6,221,005 B1 | 4/2001 | Bruckner et al. |
| 6,241,736 B1 | 6/2001 | Sater et al. |
| 6,264,676 B1 | 7/2001 | Gellman et al. |
| 6,273,852 B1 | 8/2001 | Lehe et al. |
| 6,302,840 B1 | 10/2001 | Benderev |
| 6,306,079 B1 | 10/2001 | Trabucco |
| 6,322,492 B1 | 11/2001 | Kovac |
| 6,328,686 B1 | 12/2001 | Kovac |
| 6,328,744 B1 | 12/2001 | Harari et al. |
| 6,334,446 B1 | 1/2002 | Beyar |
| 6,352,553 B1 | 3/2002 | van de Burg et al. |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,414,179 B1 | 7/2002 | Banville |
| 6,423,080 B1 | 7/2002 | Gellman et al. |
| 6,451,024 B1 | 9/2002 | Thompson et al. |
| 6,475,139 B1 | 11/2002 | Miller |
| 6,478,727 B2 | 11/2002 | Scetbon |
| 6,482,214 B1 | 11/2002 | Sidor, Jr. et al. |
| 6,491,703 B1 | 12/2002 | Ulmsten |
| 6,494,906 B1 | 12/2002 | Owens |
| 6,502,578 B2 | 1/2003 | Raz et al. |
| 6,506,190 B1 | 1/2003 | Walshe |

(56) References Cited

U.S. PATENT DOCUMENTS

| | | | |
|---|---|---|---|
| 6,530,943 B1 | 3/2003 | Hoepffner et al. |
| 6,575,897 B1 | 6/2003 | Ory |
| 6,582,443 B2 | 6/2003 | Cabak et al. |
| 6,592,515 B2 | 7/2003 | Thierfelder |
| 6,592,610 B2 | 7/2003 | Beyar |
| 6,596,001 B2 | 7/2003 | Stormby et al. |
| 6,599,235 B2 | 7/2003 | Kovac |
| 6,599,323 B2 | 7/2003 | Melican et al. |
| 6,602,260 B2 | 8/2003 | Harari et al. |
| 6,612,977 B2 | 9/2003 | Staskin |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau |
| 6,648,921 B2 | 11/2003 | Anderson |
| 6,652,450 B2 | 11/2003 | Neisz et al. |
| 6,673,010 B2 | 1/2004 | Skiba et al. |
| 6,685,629 B2 | 2/2004 | Therin |
| 6,689,047 B2 | 2/2004 | Gellman et al. |
| 6,691,711 B2 | 2/2004 | Raz |
| 6,699,175 B2 | 3/2004 | Miller |
| 6,702,827 B1 | 3/2004 | Lund |
| 6,752,814 B2 | 6/2004 | Gellman et al. |
| 6,755,781 B2 | 6/2004 | Gellman |
| 6,802,807 B2 | 10/2004 | Anderson |
| 6,830,052 B2 | 12/2004 | Carter et al. |
| 6,881,184 B2 | 4/2005 | Zappala |
| 6,884,212 B2 | 4/2005 | Thierfelder et al. |
| 6,908,425 B2 | 6/2005 | Luscombe |
| 6,908,473 B2 | 6/2005 | Skiba et al. |
| 6,911,002 B2 | 6/2005 | Fierro |
| 6,911,003 B2 | 6/2005 | Anderson et al. |
| 6,932,759 B2 | 8/2005 | Kammerer |
| 6,936,052 B2 | 8/2005 | Gellman et al. |
| 6,953,428 B2 | 10/2005 | Gellman et al. |
| 6,960,160 B2 | 11/2005 | Browning |
| 6,971,986 B2 | 12/2005 | Staskin et al. |
| 6,974,462 B2 | 12/2005 | Sater |
| 1,111,111 A1 | 1/2006 | Rosenblatt et al. |
| 6,981,944 B2 | 1/2006 | Jamiolkowski |
| 6,991,597 B2 | 1/2006 | Gellman et al. |
| 7,014,607 B2 | 3/2006 | Gellman |
| 7,025,063 B2 | 4/2006 | Snitkin |
| 7,025,772 B2 | 4/2006 | Gellman et al. |
| 7,037,255 B2 | 5/2006 | Inman |
| 7,048,682 B2 | 5/2006 | Neisz et al. |
| 7,056,333 B2 | 6/2006 | Walshe |
| 7,070,556 B2 | 7/2006 | Anderson |
| 7,070,558 B2 | 7/2006 | Gellman et al. |
| 7,083,568 B2 | 8/2006 | Neisz et al. |
| 7,083,637 B1 | 8/2006 | Tannhauser |
| 7,087,065 B2 | 8/2006 | Ulmsten et al. |
| 7,112,171 B2 | 9/2006 | Rocheleau et al. |
| 7,112,210 B2 | 9/2006 | Ulmsten et al. |
| 7,121,997 B2 | 10/2006 | Kammerer et al. |
| 7,131,943 B2 | 11/2006 | Kammerer |
| 7,131,944 B2 | 11/2006 | Jaquetin |
| 7,175,591 B2 | 2/2007 | Kaladelfos |
| 7,198,597 B2 | 4/2007 | Siegel et al. |
| 7,223,229 B2 | 5/2007 | Inman et al. |
| 7,226,407 B2 | 6/2007 | Kammerer |
| 7,226,408 B2 | 6/2007 | Harai et al. |
| 7,229,404 B2 | 6/2007 | Bouffier |
| 7,229,453 B2 | 6/2007 | Anderson |
| 7,235,043 B2 | 6/2007 | Gellman et al. |
| 7,261,723 B2 | 8/2007 | Smith et al. |
| 7,267,645 B2 | 9/2007 | Anderson et al. |
| 7,291,104 B2 | 11/2007 | Neisz et al. |
| 7,297,102 B2 | 11/2007 | Smith et al. |
| 7,299,803 B2 | 11/2007 | Kovac |
| 7,303,525 B2 | 12/2007 | Watschke et al. |
| 7,326,213 B2 | 2/2008 | Benderev et al. |
| 7,347,812 B2 | 3/2008 | Mellier |
| 7,351,197 B2 | 4/2008 | Montpetit et al. |
| 7,357,773 B2 | 4/2008 | Watschke |
| 7,364,541 B2 | 4/2008 | Chu et al. |
| 7,371,245 B2 | 5/2008 | Evans et al. |
| 7,387,634 B2 | 6/2008 | Benderev |
| 7,393,320 B2 | 7/2008 | Montpetit et al. |
| 7,407,480 B2 | 8/2008 | Staskin |
| 7,410,460 B2 | 8/2008 | Benderev |
| 7,413,540 B2 | 8/2008 | Gellman et al. |
| 7,422,557 B2 | 9/2008 | Arnal |
| 7,431,690 B2 | 10/2008 | Merade et al. |
| 7,494,495 B2 | 2/2009 | Delorme et al. |
| 7,500,945 B2 | 3/2009 | Cox |
| 7,513,865 B2 | 4/2009 | Bourne et al. |
| 7,527,588 B2 | 5/2009 | Zaddem et al. |
| 7,588,598 B2 | 9/2009 | Delorme et al. |
| 7,601,118 B2 | 10/2009 | Smith et al. |
| 7,611,454 B2 | 11/2009 | De Leval |
| 7,621,864 B2 | 11/2009 | Suslian et al. |
| 7,637,860 B2 | 12/2009 | MacLean |
| 7,645,227 B2 | 1/2010 | Smith et al. |
| 7,686,759 B2 | 3/2010 | Sater |
| 7,686,760 B2 | 3/2010 | Anderson et al. |
| 7,691,050 B2 | 4/2010 | Gellman et al. |
| 7,722,527 B2 | 5/2010 | Bouchier et al. |
| 7,722,528 B2 | 5/2010 | Arnal et al. |
| 7,740,576 B2 | 6/2010 | Hodroff |
| 7,753,839 B2 | 7/2010 | Siegel et al. |
| 7,762,942 B2 | 7/2010 | Neisz et al. |
| 7,766,926 B2 | 8/2010 | Bosley et al. |
| 7,789,821 B2 | 9/2010 | Browning |
| 7,794,385 B2 | 9/2010 | Rosenblatt |
| 7,811,223 B2 | 10/2010 | Hadroff et al. |
| 2001/0049467 A1 | 12/2001 | Lehe et al. |
| 2002/0007222 A1 | 1/2002 | Desai |
| 2002/0028980 A1 | 3/2002 | Thierfelder et al. |
| 2002/0103542 A1 | 8/2002 | Bilbo |
| 2002/0128670 A1 | 9/2002 | Ulmsten et al. |
| 2002/0147382 A1 | 10/2002 | Neisz et al. |
| 2002/0151909 A1 | 10/2002 | Gellman et al. |
| 2002/0161382 A1 | 10/2002 | Neisz |
| 2003/0004581 A1 | 1/2003 | Rousseau |
| 2003/0036676 A1 | 2/2003 | Scetbon |
| 2003/0065402 A1 | 4/2003 | Anderson et al. |
| 2003/0171644 A1* | 9/2003 | Anderson et al. ............... 600/29 |
| 2003/0176875 A1 | 9/2003 | Anderson |
| 2004/0015057 A1 | 1/2004 | Rocheleau et al. |
| 2004/0073235 A1 | 4/2004 | Lund |
| 2004/0225181 A1 | 11/2004 | Chu et al. |
| 2004/0267088 A1 | 12/2004 | Krammerer |
| 2005/0000523 A1 | 1/2005 | Beraud |
| 2005/0004427 A1 | 1/2005 | Cervigni |
| 2005/0004576 A1 | 1/2005 | Benderev |
| 2005/0008708 A1 | 1/2005 | Dai et al. |
| 2005/0038451 A1 | 2/2005 | Rao et al. |
| 2005/0055104 A1 | 3/2005 | Arnal et al. |
| 2005/0131391 A1 | 6/2005 | Chu et al. |
| 2005/0131393 A1 | 6/2005 | Chu et al. |
| 2005/0199249 A1 | 9/2005 | Karram |
| 2005/0245787 A1 | 11/2005 | Cox et al. |
| 2005/0256530 A1 | 11/2005 | Petros |
| 2005/0277806 A1 | 12/2005 | Cristalli |
| 2005/0278037 A1 | 12/2005 | Delorme et al. |
| 2005/0283189 A1 | 12/2005 | Rosenblatt et al. |
| 2006/0015010 A1 | 1/2006 | Jaffe et al. |
| 2006/0028828 A1 | 2/2006 | Phillips |
| 2006/0058575 A1 | 3/2006 | Zaddem et al. |
| 2006/0058578 A1 | 3/2006 | Browning |
| 2006/0089524 A1 | 4/2006 | Chu |
| 2006/0089525 A1 | 4/2006 | Mamo et al. |
| 2006/0122457 A1 | 6/2006 | Kovac |
| 2006/0173237 A1 | 8/2006 | Jacquetin |
| 2006/0195007 A1 | 8/2006 | Anderson |
| 2006/0195011 A1 | 8/2006 | Arnal |
| 2006/0217589 A1 | 9/2006 | Wan et al. |
| 2006/0229493 A1 | 10/2006 | Weiser et al. |
| 2006/0229596 A1 | 10/2006 | Weiser et al. |
| 2006/0252980 A1 | 11/2006 | Arnal et al. |
| 2006/0260618 A1* | 11/2006 | Hodroff et al. ............... 128/830 |
| 2006/0287571 A1 | 12/2006 | Gozzi |

(56) References Cited

U.S. PATENT DOCUMENTS

| | | |
|---|---|---|
| 2007/0015953 A1 | 1/2007 | MacLean |
| 2007/0078295 A1 | 4/2007 | Landgrebe |
| 2007/0173864 A1 | 7/2007 | Chu |
| 2008/0039678 A1 | 2/2008 | Montpetit et al. |
| 2008/0300607 A1 | 12/2008 | Meade et al. |
| 2009/0005634 A1 | 1/2009 | Rane |
| 2009/0012353 A1 | 1/2009 | Beyer |
| 2009/0221867 A1 | 9/2009 | Ogdahl et al. |
| 2009/0221868 A1 | 9/2009 | Evans |
| 2009/0259092 A1 | 10/2009 | Ogdahl et al. |
| 2010/0261950 A1 | 10/2010 | Lund et al. |

FOREIGN PATENT DOCUMENTS

| | | |
|---|---|---|
| DE | 2305815 | 2/1973 |
| DE | 4220283 C2 | 5/1994 |
| DE | 19544162 | 4/1997 |
| DE | 10211360 | 9/2003 |
| DE | 20016866 | 3/2007 |
| EA | 0470308 A1 | 2/1992 |
| EM | 1093758 A1 | 4/2001 |
| EP | 0248544 A1 | 12/1987 |
| EP | 0650703 A1 | 6/1994 |
| EP | 0643945 A2 | 7/1994 |
| EP | 0632999 A1 | 1/1995 |
| EP | 0941712 A1 | 9/1999 |
| EP | 1060714 A3 | 9/2002 |
| EP | 1342450 B1 | 9/2003 |
| EP | 1320336 B1 | 7/2005 |
| FR | 2787990 A1 | 7/2000 |
| FR | 2852813 A1 | 1/2004 |
| GB | 2268690 A | 1/1994 |
| GB | 2353220 A | 10/2000 |
| IT | 1299162 | 4/1998 |
| SU | 1225547 A1 | 4/1986 |
| SU | 1342486 A | 10/1987 |
| VN | WO02089704 A2 | 11/2002 |
| VN | WO03096928 A1 | 11/2003 |
| WO | WO9317635 A1 | 9/1993 |
| WO | WO9319678 A2 | 10/1993 |
| WO | WO9511631 A1 | 5/1995 |
| WO | WO9525469 A1 | 9/1995 |
| WO | WO9716121 A1 | 5/1997 |
| WO | WO9730638 A1 | 8/1997 |
| WO | WO9747244 A1 | 12/1997 |
| WO | WO9819606 A1 | 5/1998 |
| WO | WO9835606 A1 | 8/1998 |
| WO | WO9835616 A1 | 8/1998 |
| WO | WO9835632 A1 | 8/1998 |
| WO | WO9842261 A1 | 10/1998 |
| WO | WO9853746 A1 | 12/1998 |
| WO | WO9916381 A1 | 4/1999 |
| WO | WO9937217 A1 | 7/1999 |
| WO | WO9952450 A1 | 10/1999 |
| WO | WO9953844 A1 | 10/1999 |
| WO | WO9959477 A1 | 11/1999 |
| WO | WO0064370 A1 | 2/2000 |
| WO | WO0013601 A1 | 3/2000 |
| WO | WO0018319 A1 | 4/2000 |
| WO | WO0027304 A1 | 5/2000 |
| WO | WO0040158 A2 | 7/2000 |
| WO | WO0057812 A1 | 10/2000 |
| WO | WO0066030 A1 | 11/2000 |
| WO | WO0074594 A1 | 12/2000 |
| WO | WO0074613 A1 | 12/2000 |
| WO | WO0074633 A2 | 12/2000 |
| WO | WO0106951 A1 | 2/2001 |
| WO | WO0126581 A1 | 4/2001 |
| WO | WO0139670 A1 | 6/2001 |
| WO | WO0145588 A1 | 6/2001 |
| WO | WO0145589 A1 | 6/2001 |
| WO | WO0156499 A1 | 8/2001 |
| WO | WO0222184 A2 | 3/2002 |
| WO | WO0228312 A1 | 4/2002 |
| WO | WO0228315 A2 | 4/2002 |
| WO | WO0230293 A1 | 4/2002 |
| WO | WO0232284 A2 | 4/2002 |
| WO | WO0234124 A2 | 5/2002 |
| WO | WO0238079 A2 | 5/2002 |
| WO | WO0239890 A2 | 5/2002 |
| WO | WO02062237 A1 | 8/2002 |
| WO | WO02068563 A1 | 8/2002 |
| WO | WO02069781 | 9/2002 |
| WO | WO02071953 A2 | 9/2002 |
| WO | WO02078552 A1 | 10/2002 |
| WO | WO02091950 A1 | 11/2002 |
| WO | WO03013392 A2 | 2/2003 |
| WO | WO03017848 A1 | 3/2003 |
| WO | WO03003778 A1 | 4/2003 |
| WO | WO03028585 A2 | 4/2003 |
| WO | WO03037215 A2 | 5/2003 |
| WO | WO03041613 A1 | 5/2003 |
| WO | WO03047435 A1 | 6/2003 |
| WO | WO03047476 A1 | 6/2003 |
| WO | WO03068107 A1 | 8/2003 |
| WO | WO03073960 A1 | 9/2003 |
| WO | WO03075792 A1 | 9/2003 |
| WO | WO03086205 A2 | 10/2003 |
| WO | WO03092546 A2 | 11/2003 |
| WO | WO03096926 A1 | 11/2003 |
| WO | WO2004012625 A1 | 2/2004 |
| WO | WO2004016196 A2 | 2/2004 |
| WO | WO2004017862 A2 | 3/2004 |
| WO | WO2004034912 A1 | 4/2004 |
| WO | WO2004041115 A1 | 5/2004 |
| WO | WO2004045457 A1 | 6/2004 |
| WO | WO2005004727 A1 | 1/2005 |
| WO | WO2005037132 A2 | 4/2005 |
| WO | WO2005046511 A2 | 5/2005 |
| WO | WO2005048850 A2 | 6/2005 |
| WO | WO2005079702 A1 | 9/2005 |
| WO | WO2005087153 A2 | 9/2005 |
| WO | WO2005094741 A1 | 10/2005 |
| WO | WO2005112842 A1 | 12/2005 |
| WO | WO2005122954 A1 | 12/2005 |
| WO | WO2006007189 A1 | 1/2006 |
| WO | WO2006007190 A1 | 1/2006 |
| WO | WO2006015031 A2 | 2/2006 |
| WO | WO2006031879 A1 | 3/2006 |
| WO | WO 2006/028828 | 7/2006 |
| WO | WO2006108145 A1 | 10/2006 |
| WO | WO2007011341 A1 | 1/2007 |
| WO | WO2007014241 A1 | 2/2007 |
| WO | WO2007016083 A1 | 2/2007 |
| WO | WO2007027592 A2 | 3/2007 |
| WO | WO2007059199 A2 | 5/2007 |
| WO | WO2007081955 A1 | 7/2007 |
| WO | WO2007097994 | 8/2007 |
| WO | WO2007137226 A2 | 11/2007 |
| WO | WO2007146784 A2 | 12/2007 |
| WO | WO2007149348 A2 | 12/2007 |
| WO | WO2007149555 A2 | 12/2007 |
| WO | WO2008057261 A2 | 5/2008 |
| WO | WO2008124056 A1 | 10/2008 |
| WO | WO2009005714 A2 | 1/2009 |
| WO | WO2009017680 A2 | 2/2009 |

OTHER PUBLICATIONS

Advantage A/T™, Surgical Mesh Sling Kit, Boston Scientific, 6 pages (2002).

Albert H. Aldridge, B.S., M.D., F.A.C.S., Transplantation of Fascia for Relief of Urinary Stress Incontinence, American Journal of Obstetrics and Gynecology, V. 44, pp. 398-411, (1948).

Amundsen, Cindy L. et al., Anatomical Correction of Vaginal Vault Prolapse by Uterosacral Ligament Fixation in Women Who Also Require a Pubovaginal Sling, The Journal of Urology, vol. 169, pp. 1770-1774, (May 2003).

Araki, Tohru at al., The Loop-Loosening Procedure for Urination Difficulties After Stamey Suspension of the Vesical Neck, The Journal of Urology, vol. 144, pp. 319-323 (Aug. 1990).

Asmussen, M, et.al., Simultaneous Urethro-Cystometry With a New Technique, Scand J Urol Nephrol 10, p. 7-11 (1976).

(56) References Cited

OTHER PUBLICATIONS

Beck, Peter R. et al., Treatment of Urinary Stress Incontinence With Anterior Colporrhaphy, Obstetrics and Gynecology, vol. 69 (No. 3), pp. 289-274 (Mar. 1982).

Benderev, Theodore V., MD, A Modified Percutaneous Outpatient Bladder Neck Suspension System, Journal of Urology, vol. 152, pp. 2316-2320 (Dec. 1994).

Benderev, Theodore V., MD, Anchor Fixation and Other Modifications of Endoscopic Bladder Neck Suspension, Urology, vol. 40, No. 5, pp. 409-418 (Nov. 1992).

Bergman, Arieh et al., Three Surgical Procedures for Genuine Stress Incontinence: Five-Year Follow-Up of a Prospective Randomized Study, Am J Obstet Gynecol, vol. 173 No. 1, pp. 66-71 (Jul. 1995)

Blaivas, Jerry at al., Pubovaginal Fascial Sling for the Treatment of Complicated Stress Urinary Incontinence, The Journal of Urology, vol. 145, pp. 1214-1218 (Jun. 1991).

Blaivas, Jerry et al., Type III Stress Urinary Incontinence: Importance of Proper Diagnosis and Treatment, Surgical Forum, pp. 473-475, (1984).

Blaivas, Jerry, Commentary: Pubovaginal Sling Procedure, Experience with Pubovaginal Slings, pp. 93-101 (1990).

Boyles, Sarah Hamilton et al., Procedures for Urinary Incontinence in the United States, 1979-1997, Am J Obstet Gynecol, vol. 189, n. 1, pp. 70-75 (Jul. 2003).

Bryans, Fred E., Marlex Gauze Hammock Sling Operation With Cooper's Ligament Attachment in the Management of Recurrent Urinary Stress Incontinence, American Journal of Obstetrics and Gynecology, vol. 133, pp. 292-294.(Feb. 1979).

Burch, John C., Urethrovaginal Fixation to Cooper's Ligament for Correction of Stress Incontinence, Cystocele, and Prolapse, Am. J. Obst. & Gyn, vol. 31, pp. 281-290 (1961).

Capio™ CL—Transvaginal Suture Capturing Device—Transvaginal Suture Fixation to Cooper's Ligament for Sling Procedures, Boston Scientific, Microvasive®, 8 pages, (2002).

Cervigni, Mauro et al., The Use of Synthetics in the Treatment of Pelvic Organ Prolapse, Voiding Dysfunction and Female Urology, vol. 11, pp. 429-435 (2001).

Choe, Jong M. et al., Gore-Tex Patch Sling: 7 Years Later, Urology, vol. 54, pp. 641-646 (1999).

Cook/Ob Gyn®, Urogynecology, Copyright Cook Urological Inc., pp. 1-36 (1996).

Dargent, D. et al., Insertion of a Suburethral Sling Through the Obturator Membrane in the Treatment of Female Urinary Incontinence, Gynecol Obstet Fertil, vol. 30 pp. 576-582. (2002).

Das, Sakti et al., Laparoscopic Colpo-Suspension, The Journal of Urology, vol. 154, pp. 1119-11121 (Sep. 1995).

Debodinance, Philipp et al., "Tolerance of Synthetic Tissues in Touch With Vaginal Scars: Review to the Point of 287 Cases", Europeon Journal of Obstetrics & Gynecology and Reproductive Biology 87 (1999) pp. 23-30.

Decter, Ross M., Use of the Fascial Sling for Neurogenic Incontinence: Lessons Learned, The Journal of Urology, vol. 150, pp. 683-686 (Aug. 1993).

Delancey, John, MD, Structural Support of the Urethra as it Relates to Stress Urinary Incontinence: The Hammock Hypothesis, Am J Obstet Gynecol, vol. 170 No. 6, pp. 1713-1723 (Jun. 1994).

Delorme, Emmanuel, Trans-Obturator Sling: A Minimal Invasive Procedure to Treat Female Stress Urinary Incontinence, Progres en Urologie, vol. 11, pp. 1306-1313 (2001) English Abstract attached.

Diana, et al., Treatment of Vaginal Vault Prolapse With Abdominal Sacral Colpopexy Using Prolene Mesh, American Journal of Surgery, vol. 179, pp. 126-128, Feb. 2000.

Eglin et al., Transobturator Subvesical Mesh. Tolerance and short-term results of a 103 case continuous series, Gynecologie Obstetrique & Fertilite, vol. 31, Issue 1, pp. 14-19 (Jan. 2003).

Enzelsberger H. et el., Urodynamic and Radiologic Parameters Before and After Loop Surgery for Recurrent Urinary Stress Incontinence, Acta Obstet Gynecol Scand, 69, pp. 51-54 (1990).

Eriksen, Bjarne C. et al., Long-Term Effectiveness of the Burch Colposuspension in Female Urinary Stress Incontinence, Acta Obstet Gynecol Scand, 69, pp. 45-50, (1990).

Falconer, C. et al., Clinical Outcome and Changes in Connective Tissue Metabolism After Intravaginal Slingplasty in Stress Incontinence Women, International Urogynecology Journal, pp. 133-137, 1966.

Falconer, C. et al., Influence of Different Sling Materials of Connective Tissue Metabolism in Stress Urinary Incontinent Women International Urogynecology Journal, Supp. 2, pp. S19-S23 (2001).

Farnsworth, B.N., Posterior Intravaginal Slingplasty (Infracoccygeal Sacropexy) for Sever Posthysterectomy Vaginal Vault Prolapse—A Preliminary Report on Efficacy and Safety, Int Urogynecology J, vol. 13, pp. 4-8 (2002).

Farquhar, Cynthia M. et al., Hysterectomy Rates in the United States 1990-1997, Obstetrics & Gynecology, vol. 99, n. 2, pp. 229-234 (Feb. 2002).

Fidela, Marie R. et al., Pelvic Support Defects and Visceral and Sexual Function in Women Treated With Sacrospinous Ligament Suspension and Pelvic Reconstruction, Am J Obstet Gynecol, vol. 176, n. 6 (Dec. 1996).

Flood, C.G. et al., Anterior Colporrhaphy Reinforce With Marlex Mesh for the Treatment of Cystoceles, International Urogynecology Journal, vol. 9, pp. 200-204 (1998).

Gilja, Ivan et al., A Modified Raz Bladder Neck Suspension Operation (Transvaginal Burch), The Journal of Urology, vol. 153, pp. 1455-1457 (May 1995).

Gittes, Ruben F. et al., No-Incision Pubovaginal Suspension for Stress Incontinence, The Journal of Urology vol. 138 (Sep. 1987).

Guner, et al., Transvaginal Sacrospinous Colpopexy for Marked Uterovaginal and Vault Prolapse, Inter J of Gynec & Obstetrics, vol. 74, pp. 165-170 (2001).

Gynecare TVT Tension-Free Support for Incontinence, The tension-free solution to female Incontinence, Gynecare Worldwlde, 6 pages, (2002).

Handa, Victoria L. et al, Banked Human Fascia Lata for the Suburethral Sling Procedure: A Preliminary Report, Obstetrics & Gynecology, vol. 88 No. 6, 5 pages (Dec. 1996).

Heit, Michael et al., Predicting Treatment Choice for Patients With Pelvic Organ Prolapse, Obstetrics & Gynecology, vol. 101, n. 6, pp. 1279-1284 (Jun. 2003).

Henriksson, L. et al., A Urodynamic Evaluation of the Effects of Abdominal Urethrocystopexy and Vaginal Sling Urethroplasty in Women With Stress Incontinence, Am. J. Obstet. Gynecol. vol. 131, No. 1, pp. 77-82 (Mar. 1, 1978).

Hodgkinson, C. Paul et.al., Urinary Stress Incontinence in the Female, Department of Gynecology and Obstetrics, Henry Ford Hospital, vol. 10, No. 5, p. 493-499, (Nov. 1957).

Holschneider, C. H., et al., The Modified Pereyra Procedure in Recurrent Stress Urinary Incontinence; A 15-year Review, Obstetrics & Gynecology, vol. 83, No. 4, pp. 573-578 (Apr. 1994).

Horbach, Nicollette S., et al., Instruments and Methods, A Suburethral Sling Procedure with Potytetrafluoroethylene for the Treatment of Genuine Stress Incontinence in Patients with Low Urethral Closure Pressure, Obstetrics & Gynecology, vol. 71, No. 4, pp. 646-652 (Apr. 1998).

Ingelman-Sunberg, A. et al., Surgical Treatment of Female Urinary Stress Incontinence, Contr. Gynec. Obstet., vol. 10, pp. 51-69 (1983).

IVS Tunneller—A Universal Instrument for anterior and posterior Intra-vaginal tape placement, Tyco Healthcare, 4 pages (Aug. 2002).

IVS Tunneller—ein universelles Instrument fur die Intra Vaginal Schlingenplastik, Tyco Healthcare, 4 pages (2001).

Jeffcoate, T.N.A. et al., The Results of the Aldridge Sling Operation for Stress Incontinence, Journal of Obstetrics and Gynaecology, pp. 36-39 (1956).

Jones, N.H.J. Reay et al., Pelvic Connective Tissue Resilience Decreases With Vaginal Delivery, Menopause and Uterine Prolapse, Br J Surg, vol. 90, n. 4, pp. 466-472 (Apr. 2003).

Julian, Thomas, The Efficacy of Marlex Mesh in the Repair of Sever, Recurrent Vaginal Prolapse of the Anterior Midvaginal Wall, Am J Obstet Gynecol, vol. 175, n. 6, pp. 1472-1475 (Dec. 1996).

(56) References Cited

OTHER PUBLICATIONS

Karram, Mickey et al., Patch Procedure: Modified Transvaginal Fascia Lata Sling for Recurrent for Severe Stress Urinary Incontinence, vol. 75, pp. 461-463 (Mar. 1990).
Karram, Mickey M. et al., Chapter 19 Surgical Treatment of Vaginal Vault Prolapse, Urogynecology and Reconstructive Pelvic Surgery, (Walters & Kerram eds.) pp. 235-256 (Mosby 1999).
Kersey, J., The Gauze Hammock Sling Operation in the Treatment of Stress Incontinence, British Journal of Obstetrics and Gynaecology, vol. 90, pp. 945-949 (Oct. 1983).
Klutke, Carl et al., The Anatomy of Stress Incontinence: Magentic Resonance Imaging of the Female Bladder Neck and Urethra, The Journal of Urology, vol. 143, pp. 563-566 (Mar. 1990).
Klutke, John James et al., Transvaginal Bladder Neck Suspension to Cooper's Ligament: A Modified Pereyra Procedure, Obstetrics & Gynecology, vol. 88, No. 2, pp. 294-296 (Aug. 1996).
Klutke, John M.D. et al, The promise of tension-free vaginal tape for female SUI, Contemporary Urology, 7 pages (Oct. 2000).
Korda, A. et al., Experience With Silastic Slings for Female Urinary Incontience, Aust NZ J. Obstet Gynaecol, vol. 29, pp. 150-154 (May 1989).
Kovac, S. Robert, et al, Pubic Bone Suburethral Stabilization Sling for Recurrent Urinary Incontinence, Obstetrics & Gynecology, vol. 89, No. 4, pp. 624-627 (Apr. 1997).
Kovac, S. Robert, et al, Pubic Bone Suburethral Stabilization Sling: A Long Term Cure for SUI?, Contemporary OB/GYN, 10 pages (Feb. 1998).
Kovac, S. Robert, Follow-up of the Pubic Bone Suburethral Stabilization Sling Operation for Recurrent Urinary Incontinence (Kovac Procedure), Journal of Pelvic Surgery, pp. 156-160 (May 1999).
Kovac, Stephen Robert, M.D., Cirriculum Vitae, pp. 1-33 (Jun. 18, 1999).
Leach, Gary E., el al., Female Stress Urinary Incontinence Clinical Guidelines Panel Report on Surgical Management of Female Stress Urinary Incontinence, American Urological Association, vol. 158, pp. 875-880 (Sep. 1997).
Leach, Gary E., MD, Bone Fixation Technique for Transvaginal Needle Suspension, Urology vol. XXXI, No. 5, pp. 388-390 (May 1988).
Lichtenstein, Irving L. et al, The Tension Free Hernioplasty, The American Journal of Surgery, vol. 157 pp. 188-193 (Feb. 1989).
Loughlin, Kevin R. et al., Review of an 8-Year Experience With Modifications of Endoscopic Suspension of the Bladder Neck for Female Stress Incontinence, The Journal of Uroloyg, vol. 143, pp. 44-45 (1990).
Luber, Karl M. et al., The Demographics of Pelvic Floor Disorders; Current Observations and Future Projections, Am J Obstet Gynecol, vol. 184, n. 7, pp. 1496-1503 (Jun. 2001).
Mage, Technique Chirurgicale, L'Interpostion D'Un Treillis Synthetique Dans La Cure Par Voie Vaginale Des Prolapsus Genitaux, J Gynecol Obstet Biol Reprod, vol. 28, pp. 825-829 (1999).
Marchionni, Mauro et al., True Incidence of Vaginal Vault Prolapse—Thirteen Years of Experience, Journal of Reproductive Medicine, vol. 44 n. 8, pp. 679-684 (Aug. 199).
Marinkovic, Serge Peter et al., Triple Compartment Prolapse: Sacrocolpopexy With Anterior and Posterior Mesh Extensions, Br J Obstet Gynaecol, vol. 110, pp. 323-326 (Mar. 2003).
Marshall, Victor Fray et el. The Correction of Stress Incontinence by Simple Vesicourethral Suspension, Surgery, Gynecology and Obstetrics, vol. 86, pp. 509-518 (1949).
McGuire, Edward J. et al., Pubovaginal Sling Procedure for Stress Incontinence, The Journal of Urology, vol. 119, pp. 82-84 (Jan. 1978).
McGuire, Edward J. et al., Abdominal Procedures for Stress Incontinence, Urologic Clinics of North America, pp. 285-290, vol. 12, No. 2 May 1985.
McGuire, Edward J. et al., Experience With Pubovaginal Slings for Urinary Incontinence at the University of Michigan, Journal of Urology, vol. 138, pp. 90-93(1987).
McGuire, Edwared J. et al., Abdominal Fascial Slings, Slings, Raz Female Urology, p. 369-375 (1996).
McGuire™ Suture Buide, The McGuire™ Suture Guide, a single use instrument designed for the placement of a suburethral sling, Bard, 2 pages (2001).
McIndoe, G. A. et al., The Aldridge Sling Procedure in the Treatment of Urinary Stress Incontinence, Aust. N Z Journal of Obstet Gynecology, pp. 238-239 (Aug. 1987).
McKiel, Charles F. Jr.,et al, Marshall-Marchetti Procedure Modification, vol. 96, pp. 737-739 (Nov. 1966).
Migliari, Roberto et al., Tension-Free Vaginal Mesh Repair for Anterior Vaginal Wall Prolapse, Eur Urol, vol. 38, pp. 151-155 (Oct. 1999).
Migliari, Roberto at al., Treatment Results Using a Mixed Fiber Mesh in Patients With Grade IV Cystocele, Journal of Urology, vol. 161, pp. 1255-1258 (Apr. 1999).
Moir, J. Chesser et.al., The Gauze-Hammock Operation, The Journal of Obstetrics and Gynaecology of British Commonwealth, vol. 75 No. 1, pp. 1-9 (Jan. 1968).
Morgan, J. E., A Sling Operation, Using Marlex Polypropylene Mesh, for the Treatment of Recurrent Stress Incontinence, Am. J. Obst. & Gynecol, pp. 369-377 (Feb. 1970).
Morgan, J. E. et al., The Marlex Sling Operation for the Treatment of Recurrent Stress Urinary Incontinence: A 16-Year Review, American Obstetrics Gynecology, vol. 151, No. 2, pp. 224-226 (Jan. 1998).
Morley, George W. et al., Sacrospinous Ligament Fixations for Eversion of the Vagina, Am J Obstet Gyn, vol. 158, n. 4, pp. 872-881 (Apr. 1988).
Narik, G. et.al., A Simplified Sling Operation Suitable for Routine Use, Gynecological and Obstetrical Clinic, University of Vienna, vol. 84, No. 3 p. 400-405, (Aug. 1, 1962).
Natale, F. et al., Tension Free Cystocele Repair (TCR): Long-Term Follow-Up, International Urogynecology Journal, vol. 11, supp. 1, p. S51 (Oct. 2004).
Nichols, David H., The Mersilene Mesh Gauze-Hammock for Severe Urinary Stress Incontinence, Obstetrics and Gynecology, vol. 41, pp. 88-93 (Jan. 1973).
Nicita, Giulio, A New Operation for Genitourinary Prolapse, Journal of Urology, vol. 160, pp. 741-745 (Sep. 1998).
Niknejad, Kathleen et al., Autologous and Synthetic Urethral Slings for Female Incontinence, Urol Clin N Am, vol. 29, pp. 597-611 (2002).
Norris, Jeffrey P. et al., Use of Synthetic Material in Sling Surgery: A Minimally Invasive Approach, Journal of Endourology, vol. 10, pp. 227-230 (Jun. 1996).
O'Donnell, Pat, Combined Raz Urethral Suspension and McGuire Pubovaginal Sling for Treatment of Complicated Stress Urinary Incontinence, Journal Arkansas Medical Society, vol. 88, pp. 389-392 (Jan. 1992).
Ostergard, Donald R. et al., Urogynecology and Urodynamics Theory and Practice, pp. 569-579 (1996).
Paraiso et al., Laparoscopic Surgery for Enterocele, Vaginal Apex Prolapse and Rectocele, Int. Urogynecol J, vol. 10, pp. 223-229 (1999).
Parra, R. O., et al., Experience With a Simplified Technique for the Treatment of Female Stress Urinary Incontinence, British Journal of Urology, pp. 615-617 (1990).
Pelosi, Marco Antonio III et al., Pubic Bone Suburethral Stabilization Sling: Laparoscopic Assessment of a Transvaginal Operation for the Treatment of Stress Urinary Incontinence, Journal of Laparoendoscopic & Advaned Surgical Techniques, vol. 9, No. 1 pp. 45-50 (1999).
Pereyra, Armand J. et al, Pubourethral Supports in Perspective: Modified Pereyra Procedure for Urinary Incontinence, Obstetrics and Gynecology, vol. 59, No. 5, pp. 643-648 (May 1982).
Pereyra, Armand J., M.D., F.A.C.S., A Simplified Surgical Procedure for Correction of Stress Incontinence in Women, West.J.Surg., Obst. & Gynec, p. 223-226, (Jul.-Aug. 1959).
Peter E. Papa Petros et al., Cure of Stress Incontinence by Repair of External Anal Sphincter, Acta Obstet Gynecol Scand, vol. 69; Sup. 153, p. 75 (1990).

(56) References Cited

OTHER PUBLICATIONS

Peter Petros et al., Anchoring the Midurethra Restores Bladder-Neck Anatomy and Continence, The Lancet, vol. 354, pp. 997-998 (Sep. 18, 1999).
Petros, Peter E. Papa et al., An Anatomical Basis for Success and Failure of Female Incontinence Surgery, Scandinavian Journal of Neurourology and Urodynamics, Sup. 153, pp. 55-60 (1993).
Petros, Peter E. Papa et al., An Analysis of Rapid Pad Testing and the History for the Diagnosis of Stress Incontinence, Acta Obstet Gynecol Scand, vol. 71, pp. 529-536 (1992).
Petros, Peter E. Papa et al., An Integral Therory of Female Urinary Incontinence, Acta Obstetrlcia et Gynecologica Scandinavica, vol. 69 Sup. 153, pp. 7-31 (1990).
Petros, Peter E. Papa et al., Bladder Instability in Women: A Premature Activation of the Micturition Reflex, Scandinavian Journal of Neurourology and Urodynamics, Sup 153, pp. 235-239 (1993).
Petros, Peter E. Papa et al., Cough Transmission Ratio: An Indicator of Suburethral Vaginal Wall Tension Rather Than Urethral Closure, Acta Obstet Gynecol Scand, vol. 69, Sup 153, pp. 37-39 (1990).
Petros, Peter E. Papa et al., Cure of Urge Incontinence by the Combined Intravaginal Sling and Tuck Operation, Acta Obstet Gynecol Scand, vol. 69, Sup. 153, pp. 61-62 (1990).
Petros, Peter E. Papa et al., Further Development of the Intravaginal Slingplasty Procedure—IVS III—(With Midline "Tuck"), Scandinavian Journal of Neurourology and Urodynamics, Sup 153, p. 69-71 (1993).
Petros, Peter E. Papa et al., Medium-Term Follow-Up of the Intravaginal Slingplasty Operation Indicates Minimal Deterioration of Urinary Continence With Time, (3 pages) (1999).
Petros, Peter E. Papa et al., Non Stress Non Urge Female Urinary Incontinence—Diagnosis and Cure: A Preliminary Report, Acta Obstet Gynecol Scand, vol. 69, Sup 153, pp. 69-70 (1990).
Petros, Peter E. Papa et al., Part I: Theoretical, Morphological, Radiographical Correlations and Clinical Perspective, Scandinavian Journal of Neurourology and Urodynamics, Sup 153, pp. 5-28 (1993).
Petros, Peter E. Papa et al., Part II: The Biomechanics of Vaginal Tissue and Supporting Ligaments With Special Relevance to the Pathogenesis of Female Urinary Incontinence, Scandinavian Journal of Neurourology and Urodynamics, Sup 153, pp. 29-40 plus cover sheet (1993).
Petros, Peter E. Papa et al., Part III: Surgical Principles Deriving From the Theory, Scandinavian Journal of Neurourology and Urodynamics, Sup 153, pp. 41-52 (1993).
Petros, Peter E. Papa et al., Part IV: Surgical Appliations of the Theory—Development of the Intravaginal Sling Pklasty (IVS) Procedure, Scandinavian Journal of Neurourology and Urodynamics, Sup 153, pp. 53-54 (1993).
Petros, Peter E. Papa et al., Pinch Test for Diagnosis of Stress Urinary Incontinence, Acta Obstet Gynecol Scand, vol. 69, Sup 153, pp. 33-35 (1990).
Petros, Peter E. Papa et al., Pregnancy Effects on the Intravaginal Sling Operation, Acta Obstet Gynecol Scand, vol. 89, Sup 153, pp. 77-79 (1990).
Petros, Peter E. Papa et al., The Autogenic Ligament Procedure: A Technique for Planned Formation of an Artificial Neo-Ligament, Acta Obstet Gynecol Scand, vol. 69, Sup 153, pp. 43-51 (1990).
Petros, Peter E. Papa et al., The Combined Intravaginal Sling and Tuck Operation an Ambulatory Procedure for Cure of Stress and Urge Incontinence, Acta Obstet Gynecol Scand, vol. 69, Sup 153, pp. 53-59 (1990).
Petros, Peter E. Papa et al., The Development of the Intravaginal Slingplasty Procedure: IVS II—(With Bilateral "Tucks"), Scandinavian Journal of Neurourology and Urodynamics, Sup 153, pp. 61-67 (1993).
Petros, Peter E. Papa et al., The Free Graft Procedure for Cure of the Tethered Vagina Syndrome, Scandinavian Journal of Neurourology and Urodynamics, Sup 153, pp. 85-87(1993).
Petros, Peter E. Papa et al., The Further Development of the Intravaginal Slingplasty Procedure—IVS IV—(With "Double Breasted" Unattached Vaginal Flap Repair and "Free" Vaginal Tapes), Scandinavian Journal of Neurourology and Urodynamics, Sup 153, p. 73-75 (1993).
Petros, Peter E. Papa et al., The Further Development of the Intravaginal Slingplasty Procedure—IVS V—(With "Double Breasted" Unattached Vaginal Flap Repair and Permanent Sling)., Scandinavian Journal of Neurourology and Urodynamics, Sup 153, pp. 77-79 (1993).
Petros, Peter E. Papa et al., The Intravaginal Slingplasty Operation, A Minimally Invasive Technique for Cure of Urinary Incontinence in the Female, Aust. NZ J Obstet Gynaecol, vol. 36, n. 4, pp. 453-481 (1996).
Petros, Peter E. Papa et al., The Intravaginal Slingplasty Procedure: IVS VI—Further Development of the "Double Breasted" Vaginal Flap Repair—Attached Flap, Scandinavian Journal of Neurourology and Urodynamics Sup 153, pp. 81-84 (1993).
Petros, Peter E. Papa et al., The Posterior Fornix Syndrome: A Multiple Symptom Complex of Pelvic Pain and Abnormal Urinary Symptoms Deriving From Laxity in the Posterior Fornix of Vagina, Scandinavian Journal of Neurourology and Urodynamics. Sup 153, pp. 89-93 (1993).
Petros, Peter E. Papa et el., The Role of a Lax Posterior Vaginal Fornix in the Causation of Stress and Urgency Symptoms: A Preliminary Report, Acta Obstet Gynecol Scand, vol. 89, Sup 153, pp. 71-73 (1990).
Petros, Peter E. Papa et al., The Tethered Vagina Syndrome, Post Surgical Incontinence I-Plasty Operation for Cure, Acta Obstet Gynecol Scand, vol. 69, Sup 153, pp. 63-67 (1990).
Petros, Peter E. Papa et al., The Tuck Procedure: A Simplified Vaginal Repair for Treatment of Female Urinary Incontinence, Acta Obstet Gynecol Scand, vol. 69, Sup 153, pp. 41-42 (1992).
Petros, Peter E. Papa et al., Urethral Pressure Increase on Effort Originates From Within the Urethra, and Continence From Musculovaginal Closure, Scandinavian Journal of Neurourology and Urodynamics, pp. 337-350 (1995).
Petros, Peter E. Papa, Development of Generic Models for Ambulatory Vaginal Surgery—Preliminary Report,International Urogynecology Journal, pp. 20-27 (1998).
Petros, Peter E. Papa, New Ambulatory Surgical Methods Using an Anatomical Classification of Urinary Dysfunction Improve Stress, Urge and Abnormal Emptying, Int. Urogynecology Journal Pelvic Floor Dystfunction, vol. 8 (5), pp. 270-278, (1997).
Petros, Peter E. Papa, Vault Prolapse II: Restoration of Dynamic Vaginal Supports by Infracoccygeal Sacropexy, an Axial Day-Case Vaginal Procedure, Int. Urogynecol J, vol. 12, pp. 296-303 (2001).
Rackley, Raymond R. et al., Tension-Free Vaginal Tape and Percutaneous Vaginal Tape Sling Procedures, Techniques in Urology, vol. 7, No. 2 pp. 90-100 (2001).
Rackley, Raymond R. M.D., Synthetic Slings: Five Steps for Successful Placement, Urology Times, p. 48,48,49 (Jun. 2000).
Raz, Shlomo, et al., The Raz Bladder Neck Suspension Results in 206 Patients, The Journal of Urology, pp. 845-846 (1992).
Raz, Shlomo, Female Urology, pp. 80-86, 388-398, 435-442 (1996).
Raz, Shlomo, MD, Modified Bladder Neck Suspension for Female Stress Incontinence, Urology, vol. XVII, No. 1, pp. 82-85 (Jan. 1981).
Richardson, David A. et al., Delayed Reaction to the Dacron Buttress Used in Urethropexy, The Journal of Reproductive Medicine, pp. 689-692, vol. 29, No. 9 (Sep. 1984).
Richter, K., Massive Eversion of the Vagina: Pathogenesis, Diagnosis and Therapy of the "True" Prolapse of the Vaginal Stump, Clin obstet gynecol, vol. 25, p.p 897-912 (1982).
Ridley, John H., Appraisal of the Goebell-Frangenheim-Stoeckel Sling Procedure, American Journal Obst & Gynec., vol. 95, No. 5, pp. 741-721 (Jul. 1, 1986).
Roberts, Henry, M.D., Cystourethrography in Women, Deptment of Obstetrics and Gynaecology, University of Liverpool, May 1952, vol. XXXV, No. 293, pp. 253-259.
SABRE™ Bioabsorbable Sling, Generation Now, Mentor, 4 pages (May 2002).
SABRE™ Surgical Procedure, Mentor, 6 pages. (Aug. 2002).
Sanz, Luis E. et al., Modification of Abdominal Sacrocolpopexy Using a Suture Anchor System, The Journal of Reproductive Medicine, vol. 48, n. 7, pp. 400-500 (Jul. 2003).

(56) References Cited

OTHER PUBLICATIONS

Seim, Arnfinn et al., A Study of Female Urinary Incontinence in General Practice—Demography, Medical History, and Clinical Findings, Scand J Urol Nephrol, vol. 30, pp. 465-472 (1996).
Sergent, F. et al., Prosthetic Restoration of the Pelvic Diaphragm in Genital Urinary Prolapse Surgery: Transobturator and Infacoccygeal Hammock Technique, J Gynecol Obstet Biol Reprod, vol. 32, pp. 120-126 (Apr. 2003).
Sloan W. R. et al., Stress Incontinence of Urine: A Retrospective Study of the Complications and Late Results of Simple Suprapubic Suburethral Fascial Slings, The Journal of Urology, vol. 110, pp. 533-536 (Nov. 1973).
Spencer, Julia R., et al., A Comparison of Endoscopic Suspension of the Vesical Neck With Suprapubic Vesicourethropexy for Treatment of Stress Urinary Incontinence, The Journal of Urology, vol. 137, pp. 411-415 (Mar. 1987).
Stamey, Thomas A., M.D., Endoscopic Suspension of the Vesical Neck for Urinary Incontinence in Females, Ann. Surgery, vol. 192 No. 4, pp. 465-471 (Oct. 1980).
Stanton, Stuart L., Suprapubic Approaches for Stress Incontinence in Women, Journal of American Geriatrics Society, vol. 38, No. 3, pp. 348-351 (Mar. 1990).
Stanton, Stuart, Springer-Veglag, Surgery of Female Incontinence, pp. 105-113 (1986).
Staskin et al., A Comparison of Tensile Strength among Three Preparations of Irradiated and Non-Irradiated Human Fascia Lata Allografts (2 pages).
Staskin, David R. et al., The Gore-Tex Sling Procedure for Female Sphincteric Incontinence: Indications, Technique and Results, World Journal of Urology; vol. 15, pp. 295-299 (1997).
Studdiford, William E., Transplantation of Abdominal Fascia for the Relief of Urinary Stress Incontinence, American Journal of Obstetrics and Gynecology, pp. 784-775 (1944).
Subak, Leslee L. et al., Cost of Pelvic Organ Prolapse Surgery in the United States, Obstetrics & Gynecology, vol. 98, n. 4, pp. 646-651 (Oct. 2001)
Sullivan, Eugene S. et al., Total Pelvic Mesh Repair a Ten-Year Experience, Dis. Colon Rectum, vol. 44, No. 6, pp. 857-863 (Jun. 2001).
Swift, S.E., et al., Case-Control Study of Etiologic Factors in the Development of Sever Pelvic Organ Prolapse, Int Urogynecol J. vol. 12, pp. 187-192 (2001).
TVT Tension-free Vaginal Tape, Gynecare, Ethicon, Inc., 23 pages (1999).
Ulmsten, U. et al., A Multicenter Study of Tension-Free Vaginal Tape (TVT) for Surgical Treatment of Stress Urinary Incontinence, International Urogynecology Journal, vol. 9, pp. 210-213 (1998).
Ulmsten, U. et al., An Ambulatory Surgical Procedure Under Local Anesthesia for Treatment of Female Urinary Incontinence, International Urogynecology Journal, vol. 7 pp. 81-86 (May 1996).
Ulmsten, U., Female Urinary Incontinence—A Symptom, Not a Urodynamic Disease. Some Theoretical and Practical Aspects on the Diagnosis a Treatment of Female Urinary Incontinence, International Urogynecology Journal, vol. 6, pp. 2-3 (1995).
Ulmsten Ulf et al., A Three Year Follow Up of Tension Free Vaginal Tape for Surgical Treatment of Female Stress Urinary Incontinence, British Journal of Obstetrics and Gynaecology, vol. 106, pp. 346-350 (1999).
Ulmsten, Ulf et al., Different Biochemical Composition of Connective Tissue in Continent, Acta Obstet Gynecol Scand, pp. 455-457 (1987).
Ulmsten, Ulf et al., Intravaginal Slingplasty (IVS): An Ambulatory Surgical Procedure for Treatment of Female Urinary Incontinence, Scand J Urol Nephrol, vol. 29, pp. 75-82 (1995).
Ulmsten, Ulf et al., The Unstable Female Urethra, Am. J. Obstet, Gynecol., vol. 144 No. 1, pp. 93-97 (Sep. 1, 1982).
UroMed Access Instrument System for the Sub-urethral Sling Procedure Catalog No. 120235, Directions for Use, (3 pages).
Vesica® Percutaneous Bladder Neck Stabilization Kit, A New Approach to Bladder Neck Suspenison, Microvasive® Boston Scientific Corporation, 4 pages (1995).
Vesica® Sling Kits, Simplifying Sling Procedures, Microvasive® Boston Scientific Corporation, 4 pages (1998).
Villet, R., Reponse De R. Villet A L'Article De D. Dargent et al., Gynécolgie Obstétrique & Fertilité, vol. 31, p. 96 (2003).
Visco, Anthony G. et al., Vaginal Mesh Erosion After Abdominal Sacral Colpopexy, Am J Obstet Gynecol, vol. 184, n. 3, pp. 297-302.
Walters, Mark D., Percutaneous Suburethral Slings: State of the Art, Presented at the conference of the American Urogynecologic Society, Chicago, 29 pages (Oct. 2001).
Waxman, Steve et al., Advanced Urologic Surgery for Urinary Incontinence, The Female Patent, pp. 93-100, vol. 21 (Mar. 1996).
Weber, Anne M. et al., Anterior Vaginal Prolapse: Review of Anatomy and Techniques of Surgical Repair, Obstetrics and Gynecology, vol. 89, n. 2, pp. 311-318 (Feb. 1997).
Webster, George et al., Voiding Dysfunction Following Cystourethropexy: Its Evaluation and Management, The Journal of Urology, vol. 144, pp. 670-673 (Sep. 1990).
Winter, Chester C., Peripubic Urethropexy for Urinary Stress Incontinence in Women, Urology, vol. XX, No. 4, pp. 408-411 (Oct. 1982).
Winters et al., Abdominal Sacral Colpopexy and Abdominal Enterocele Repair in the Management of Vaginal Vault Prolapse, Urology, vol. 66, supp. 6A, pp. 55-63 (2000).
Woodside, Jeffrey R. et al., Suprapubic Endoscopic Vesical Neck Suspension for the Management of Urinary Incontinence in Myelodysplastic Girls, The Journal of Urology, vol. 135, pp. 97-99 (Jan. 1986).
Zacharin, Robert et al., Pulsion Enterocele: Long-Term Results of an Abdominoperineal Technique, Obstetrics & Gynecology, vol. 55 No. 2, pp. 141-148 (Feb. 1980).
Zacharin, Robert, The Suspensory Mechanism of the Female Urethra, Journal of Anatomy, vol. 97, Part 3, pp. 423-427 (1963).
Zimmern, Phillippe E. et al., Four-Corner Bladder Neck Suspension, Vaginal Surgery for the Urologist, vol. 2, No. 1, pp. 29-36 (Apr. 1994).
Mouly, Patrick et al., Vaginal Reconstruction of a Complete Vaginal Prolapse: The Trans Obturator Repair, Journal of Urology, vol. 169, p. 183 (Apr. 2003).
Pourdeyhimi, B, Porosity of Surgical Mesh Fabrics: New Technology, J. Biomed. Mater. Res.: Applied Biomaterials, vol. 23, No. A1, pp. 145-152 (1989).
Drutz, H.P. et al., Clinical and Urodynamic Re-Evaluation of Combined Abdominovaginal Marlex Sling Operations for Recurrent Stress Urinary Incontinence, International Urogynecology Journal, vol. 1, pp. 70-73 (1990).
Petros, Papa PE et al., An Integral Theory and Its Method for the Diagnosis and Management of Female Urinary Incontinence, Scandinavian Journal of Urology, and Nephrology, Supplement 153: p. 1 (1993).
Mentor Porges, Uratape, ICS/IUGA Symp, Jul. 2002.
Kettel, L. Michael et al., An Anatomical Evaluation of the Sacrospinous Ligament Colpopexy, Surg. Gynecol. Obstet. 168(4):318-22 Apr. 1989.
Flynn, B.J. et al., Surgical Management of the Apical Vaginal Defect, Curr. Opin. Urol. 12(4):353-58, Jul. 2002.
Buller, J.L. et al., Uterosacral Ligament; Description of Anatomic Relationships to Optimize Sergical Safety, Obstet. Gynecol. 97:873-79, 2001.
Brochure, "GPS for Pelvic Floor Repair," Gynecare Prolift, 6 pages, 2005.

* cited by examiner

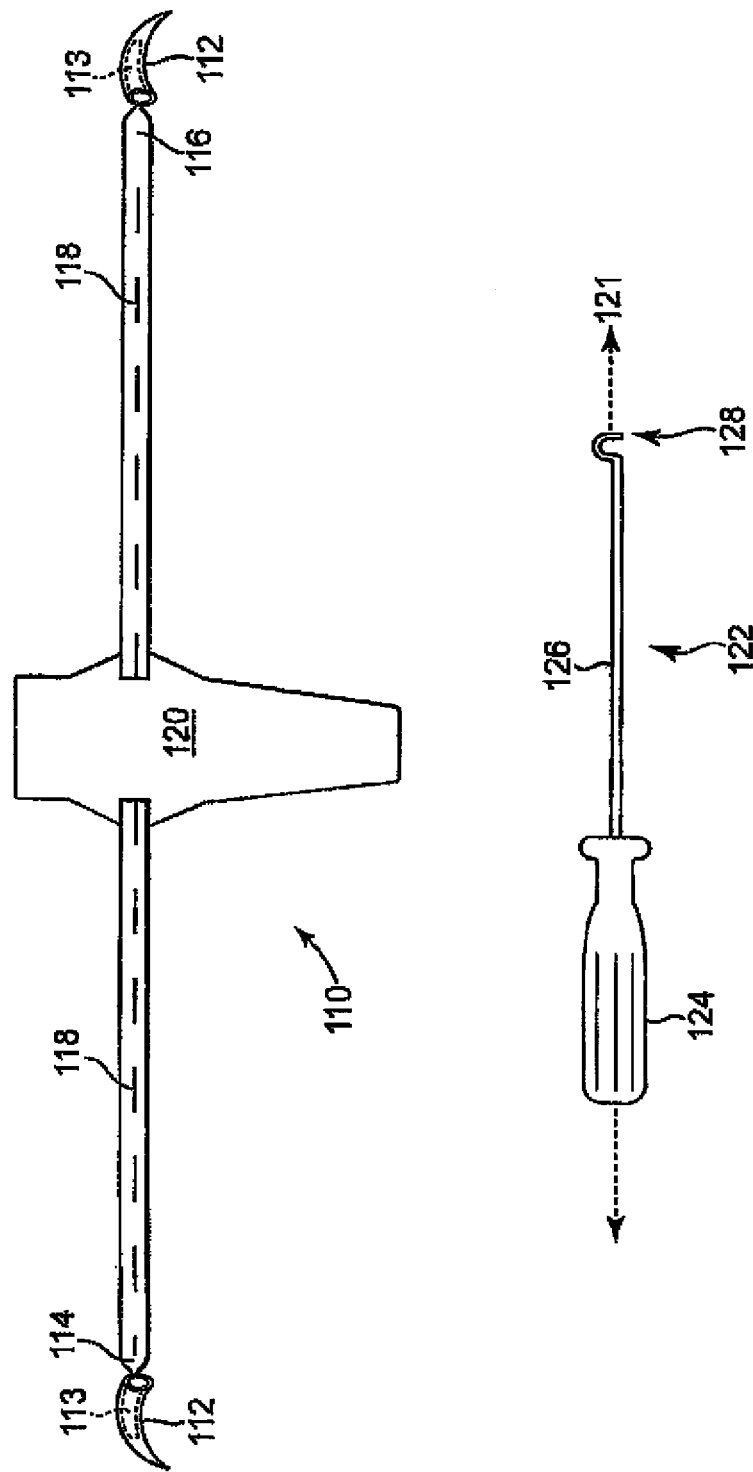

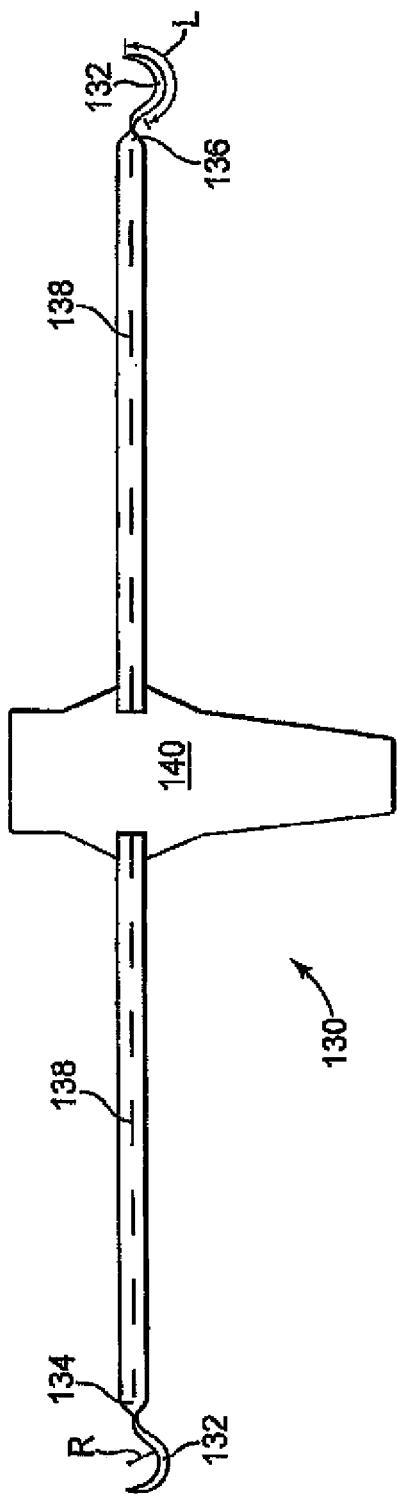

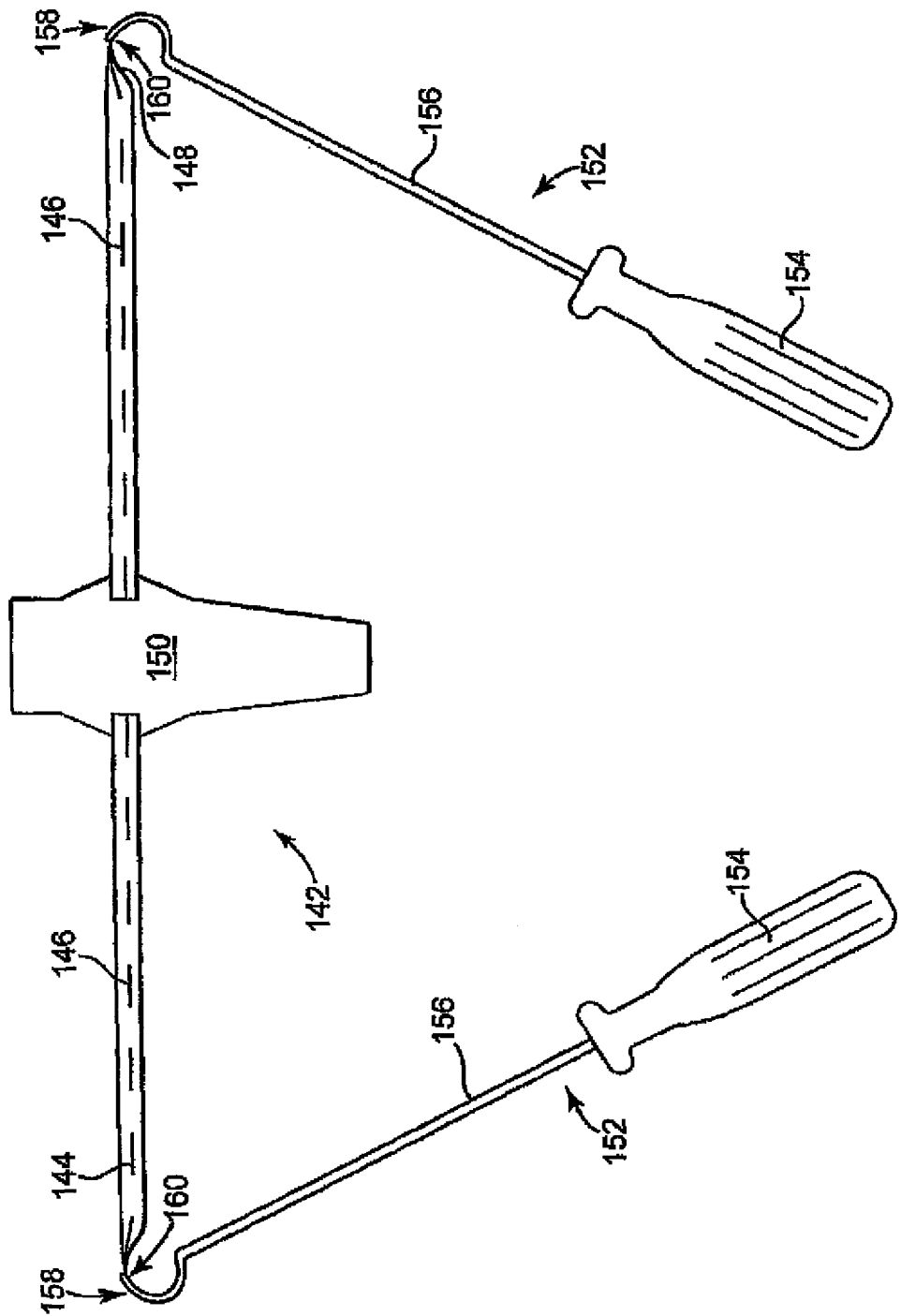

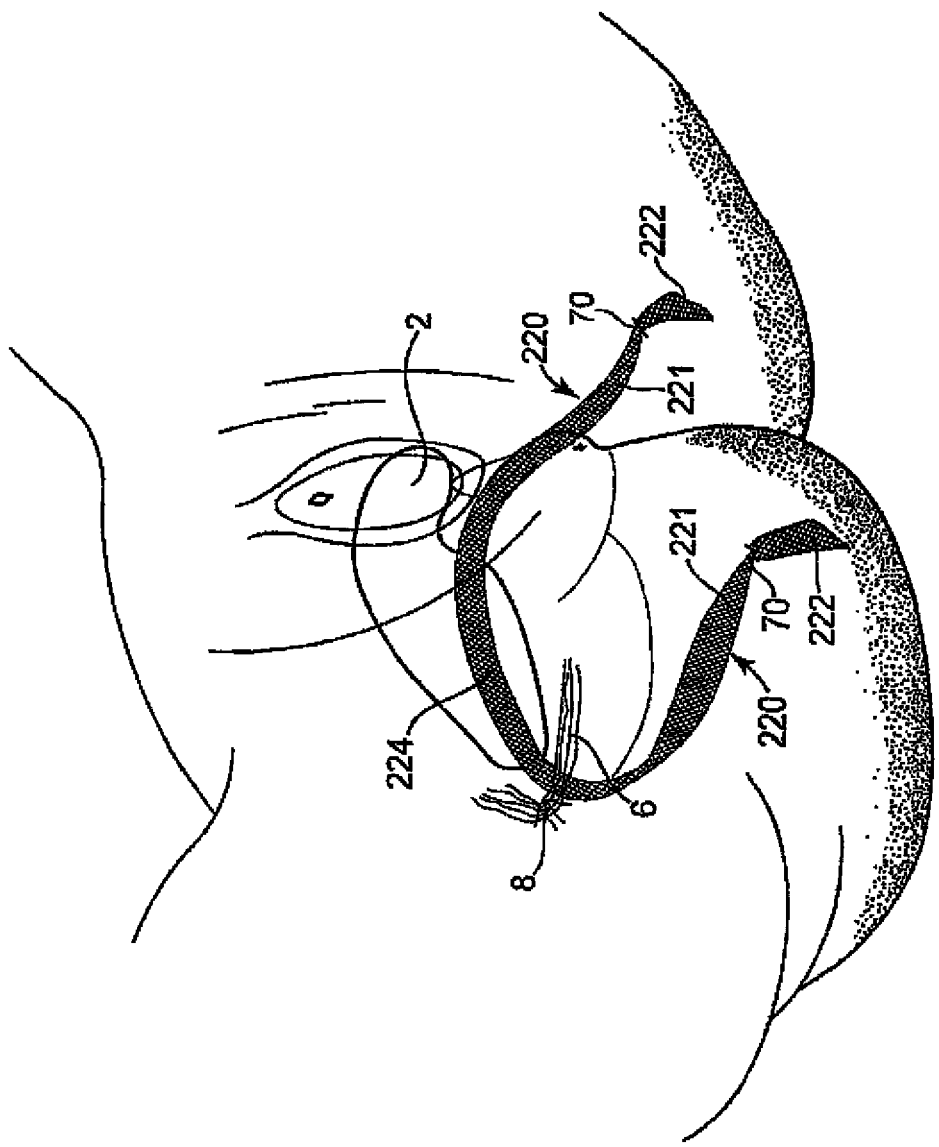

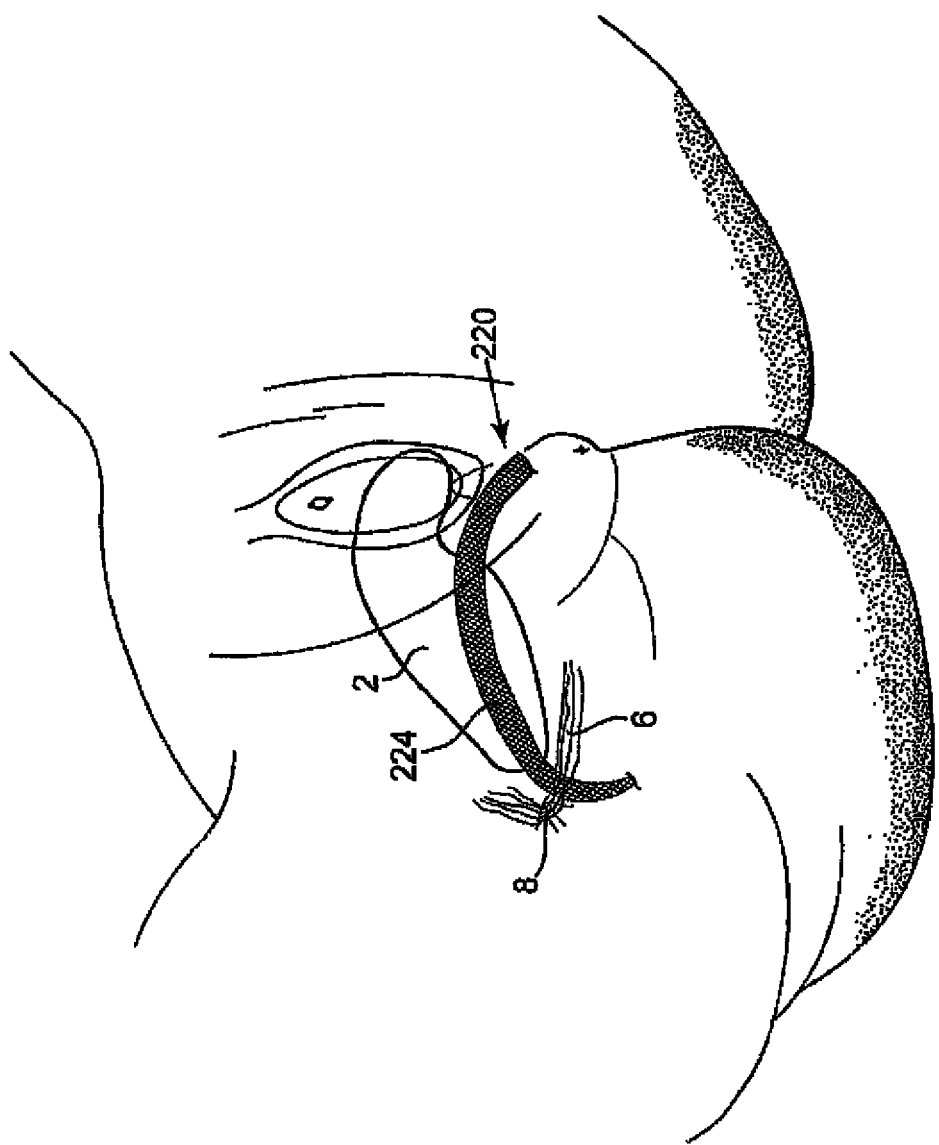

METHODS AND SYSTEMS FOR TREATMENT OF PROLAPSE

PRIORITY CLAIM

This application is a continuation of U.S. application Ser. No. 14/025,988, filed Sep. 13, 2013, which is a continuation of U.S. application Ser. No. 11/989,256, filed Feb. 24, 2009, now U.S. Pat. No. 8,535,217, which claims the benefit from International No. PCT/US2006/028828, which was granted an International Filing date of Jul. 25, 2006, which in turns claims priority under 35 USC §119(e) from U.S. Provisional Patent Application Ser. No. 60/702,704, filed on Jul. 26, 2005, by James E. Cox and titled CONNECTORLESS IMPLANT SYSTEM; 60/702,705, filed on Jul. 26, 2005, by Guillermo Wiley Davila et al. and titled TRANSVAGINAL SYSTEM FOR APICAL SUPPORT; and 60/702,700, filed on Jul. 26, 2005, by James E. Cox et al. and titled METHODS AND SYSTEMS FOR TRANSVAGINAL TREATMENT OF PROLAPSE, which applications are incorporated herein by reference in their entireties.

FIELD OF THE INVENTION

Described herein are features of surgical articles, surgical methods, and surgical tools, for use in the field of pelvic surgery, e.g., to install support devices for use in treating vaginal prolapse.

BACKGROUND

Medical conditions involving pelvic prolapse are conditions of great importance. An aging population can be prone to such conditions. Pelvic prolapse develops when intra-abdominal pressure, muscle failure, a surgical procedure such as a hysterectomy, or other factors, allow or cause a tissue of a pelvic organ such as the vagina to become displaced. Within the general category of pelvic organ prolapse, specific types include vault prolapse (apical); cystocele (anterior); rectocele and enterocele (posterior); and combinations of these.

Various techniques have been designed to correct or ameliorate prolapse and prolapse symptoms, with varying degrees of success. Nonsurgical treatments involve measures to improve the factors associated with prolapse, including treating chronic cough, obesity, and constipation. Other non-surgical treatments may include pelvic muscle exercises or supplementation with estrogen.

A variety of surgical procedures have also been attempted for the treatment of prolapse. See for example U.S. patent application Ser. No. 10/834,943, entitled "Method and Apparatus for Treating Pelvic Organ Prolapse," filed Apr. 30, 2004, and Ser. No. 10/306,179, entitled "Transobturator Surgical Articles and Methods," filed Nov. 27, 2002, the entireties of each of these two patent applications being incorporated herein by reference. Such patent applications describe articles and methods for treating pelvic organ prolapse by use of a support member for supporting specific tissue. Application Ser. No. 10/834,943, for example, discusses a support member that includes a central tissue support portion and two end (extension) portions, and related methods for implantation. The central tissue support portion can be attached at tissue of a vaginal vault. The end portions of the support member are then positioned through respective tissue pathways extending to an external incision at the perirectal region, to place the support member in a therapeutic position.

Methods of supporting vaginal tissue to treat vaginal prolapse can be differentiated in terms of the location of implanted materials or anatomical tissue used to support the vaginal tissue. One current method of treating posterior vaginal tissue prolapse involves the use of an intravaginal slingplasty ("IVS") tunneler device. Methods of treating prolapse using an IVS tunneler involve supporting vaginal tissue by attaching a portion of a surgical implant to vaginal tissue and passing another portion of the implant through the iliococcygeus muscle below the white line, for support. A different technique, known as sacrospinous ligament fixation, involves supporting vaginal tissue by attachment to the sacrospinous ligaments. Both of these methods have drawbacks, such as not providing completely correct anatomical support for the vagina. Attaching vaginal tissue to the sacrospinous ligaments can pull the vagina down toward the pelvic floor. The use of an IVS tunneler to pass an implant through the iliococcygeous muscle allows for support from a location higher up in the anatomy, but still not an anatomically correct location.

SUMMARY

The invention relates to transvaginal methods of treating posterior vaginal prolapse, and surgical devices. Embodiments relate to methods, tools, and surgical systems useful for transvaginal placement of an implant (e.g., a synthetic mesh implant or an implant that contains a combination of synthetic and biologic materials) in a position to support posterior tissue of the vagina, wherein the implant passes bi-laterally through opposing tissue paths that each include passage at a region of the arcus tendineus, e.g., near the ischial spine.

Some embodiments of methods may involve an external incision at a perirectal region, to place an extension portion of an implant, while alternate embodiments to not require and can avoid an external incision. The implant can be introduced to the pelvic region transvaginally; transvaginally attached to tissue of the vaginal vault for support; and then distal ends of the implant can be passed bilaterally near a region of each arcus tendineus (e.g., near both of the patient's ischial spines), as described, using a transvaginal procedure.

The tissue path through a region of the arcus tendineus can result in benefits including proper anatomical positioning of the supported vaginal tissue, and fixation of the implant in tissue near the arcus tendineus due to tissue ingrowth. Additionally, exemplary transvaginal methods can allow for the location of extension portions to be adjusted by movement of the extension portion extending through the tissue path, e.g., through a tissue path that surrounds the arcus tendineus.

According to certain embodiments an implant can be used to treat vaginal vault prolapse. The support member can include a tissue support portion that can be attached to tissue of the vaginal vault and two end portions attached to the tissue support portion. The implant can be used to place vaginal tissue in a therapeutic position for treatment of vaginal vault prolapse by attaching the tissue support portion to tissue of the vaginal vault, and attaching the end portions to separate locations for positioning or supporting the prolapsed tissue.

Exemplary implants, methods, tools, and systems provide anatomical support to treat vaginal prolapse (e.g., vaginal vault prolapse, enterocele, and rectocele) by using a supportive implant attached to vaginal tissue, that passes from posterior vaginal tissue to a location in a region of the arcus tendineus ("white line"), e.g., near the ischial spine. The implant can pass from the point of attachment at the vaginal tissue, through a tissue path that includes passage through tissue at the immediately anterior edge of the ischial spine and at the level of the ischial spine near the connection of the ischial spine to the arcus tendineus, and above or below the arcus tendineus.

As used herein, the terminology that refers to positions "above" the white line refers to anatomy that includes the obturator internus muscle, and references to positions "below" the white line refer to anatomy that includes the iliococcygeus muscle. Stated differently, embodiments of the invention involve a tissue path that is defined to include a curved-rectangular-shaped area above and below the curved arcus tendineus. The region includes a specific region having a height extending from 2 inches above to 2 inches below the arcus tendineus, and a length starting at the ischial spine and extending 3 centimeters to the anterior of the ischial spine.

In one aspect, the invention relates to a method of supporting posterior vaginal tissue. The method includes: providing an implant comprising a tissue support portion and an extension portion extending from the tissue support portion, creating a vaginal incision, transvaginally contacting the support portion with posterior vaginal tissue, transvaginally producing a tissue path between the position of the tissue support portion and a region of the arcus tendineus, and transvaginally extending the extension portion through the tissue path.

In another aspect, the invention relates to a pelvic implant assembly that includes: an implant comprising supportive portions comprising a tissue support portion, and elongate extension portions extending from of the tissue support portion; and an insertion tool at a distal end of an extension portion, the insertion tool comprising a curved portion sized and shaped to be used in a transvaginal procedure to define a tissue path that exits the pelvic floor region in a region of the arcus tendineus, partially extends around an arcus tendineus, and re-enters the pelvic floor.

BRIEF DESCRIPTION OF THE DRAWINGS

FIG. 4 illustrates an exemplary system of the invention including an exemplary tool and an exemplary implant with attached dilators.

FIG. 5 illustrates an exemplary implant according to the invention.

FIG. 6 illustrates an exemplary implant assembly according to the invention, including an implant and attached insertion tools.

FIG. 7 illustrates an exemplary implanted pelvic implant according to the invention.

FIG. 7A illustrates an exemplary implanted pelvic implant according to the invention.

DETAILED DESCRIPTION

Figure 1:
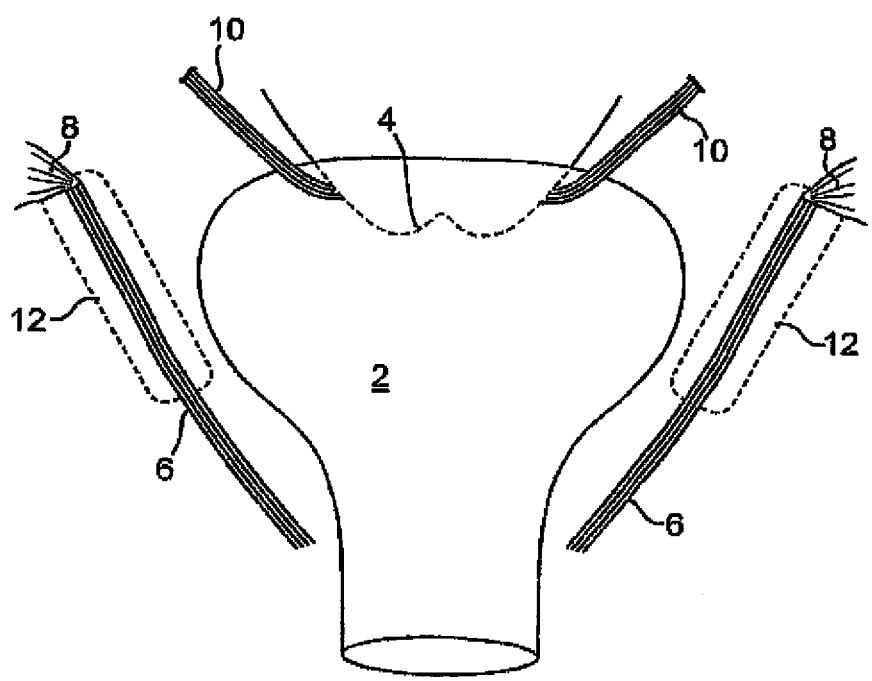
FIG. 1 illustrates anatomy relevant to the invention, including specific pelvic anatomy.

According the invention, surgical implants can be used to treat conditions of vaginal prolapse. Also contemplated herein are various features of surgical implants, surgical tools, systems that include implant and tool, and surgical methods. The implants and tools are useful for treating conditions of vaginal prolapse including vaginal vault prolapse, but will also be appreciated to be useful for treating other conditions of pelvic tissue prolapse.

In general, the invention relates to methods, tools, and systems useful for attaching one portion of a surgical implant to pelvic tissue such as vaginal tissue and passing another portion of the implant through a tissue path that includes tissue in the region of the arcus tendineus or "white line," preferably near the ischial spine.

The location of this tissue path passing through a region of the arcus tendineus or "white line" can result in improved anatomical correctness of the position of supported vaginal tissue. The location in the region of the white line can provide a proper axis for supported vaginal tissue, higher than support provided by alternate methods of treating vaginal prolapse such as those that involve sacrospinous ligament fixation or use of the IVS tunneler, which alternate methods would typically produce a tissue path more directly through the buttocks. A location in the region of the arcus tendineus, e.g., above the arcus tendineus, does not cause vaginal tissue to be pulled down toward the pelvic floor as with attachment to the sacrospinous ligaments. Also, a better vaginal length can result compared to the use of an IVS tunneler, because the support is located closer to the ischial spine.

Also advantageously, a tissue path can be one that wraps around the outside portion (relative to the region of the pelvic floor) of the arcus tendineus, meaning that an extension portion of an implant exits the pelvic region near the arcus tendineus (either above or below the arcus tendineus), continues along a path that wraps or bends around the white line, then re-enters the pelvic region on the other side of the white line; i.e., below or above the arcus tendineus, whichever is opposite of the direction of entry. The tissue path can include a relatively sharp turning radius to place the extension portion near the arcus tendineus. By extending around the white line, the extension portion contacts tissue that surrounds the white line and can become ingrown into that tissue. This ingrowth can provide fixation of the extension portion into the tissue. During the procedure the placement of the extension portion and implant can be adjusted by manipulating the extension portion from the pelvic region side, after passing the extension portion around the arcus tendineus. Specifically, the extension portion will include two portions within the pelvic region, and those two portions can be manipulated to adjust the position of one or more of the extension portion, a central portion of an implant, and tissue attached to a central portion of the implant.

FIG. 1 schematically illustrates a top view of anatomy of vagina and nearby tissue. Vagina 2 and cervix 4 are schematically illustrated in relation to arcus tendineus or "white line" 6, ischial spine 8, and uterosacral ligaments 10. An exemplary region of a tissue path according to the invention, a region of the arcus tendineus, 6, is illustrated as an approximately-rectangular regions 12 (shown by dashed lines—one on each side of the pelvic region). Each region 12 includes area above and below arcus tendineus, 6, starting at ischial spine 8 and extending in an anterior direction along the length of the arcus tendineus. Although obturator internus and iliococcygeus muscles are not shown in FIG. 1, region 12 is located to include or be adjacent to the obturator internus muscle (above the white line) and the iliococcygeus muscle (below the white line); a tissue path that passes through region 12 also passes through obturator internus muscle or iliococcygeous muscle.

A preferred example of a region of the arcus tendineus, e.g., as illustrated as region 12, can be defined as a curved-rectangular-shaped area defined to include a region that extends 2 centimeters above and 2 centimeters below (e.g., 1 centimeter above and 1 centimeter below) the arcus tendineus and that has a length starting at the ischial spine and extending in an anterior direction along the arcus tendineus, e.g., a distance of up to about 3 centimeters anterior of the ischial spine (e.g., up to about 1 centimeter anterior to the ischial spine). A particularly preferred tissue path can be very near or as close as possible to the ischial spine and either above or below the arcus tendineus, such as through tissue at the immediately anterior edge of the ischial spine and at the level of the ischial spine near the connection of the ischial spine to the arcus tendineus; dimensions can be 0.5 or 1 centimeter above or below the arcus tendineus, and 0.5 or 1 centimeter anterior to the ischial spine along the arcus tendineus.

Figure 2:
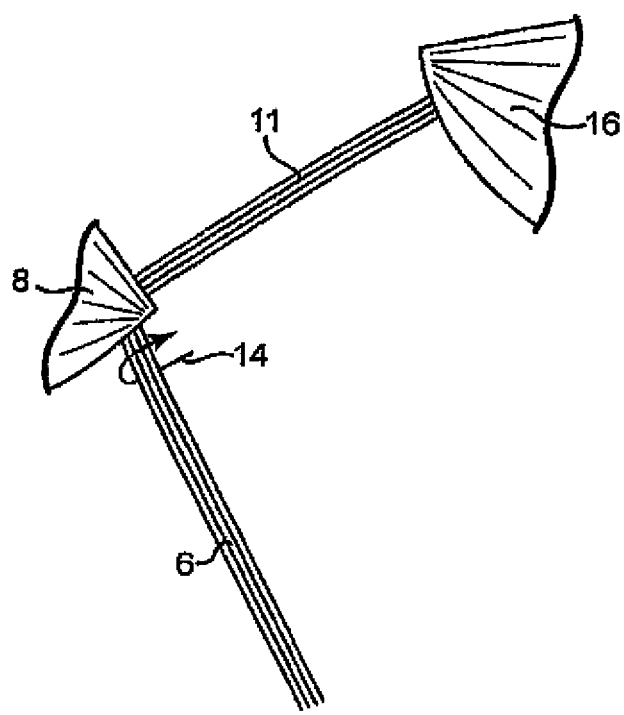
FIG. 2 illustrates anatomy relevant to the invention, including specific pelvic anatomy.

FIG. 2, a top view of pelvic features, schematically illustrates sacrospinous ligament 11, arcus tendineus 6, ischial spine 8, sacrum 16, and exemplary tissue path 14 illustrated as circular line 14 passing around an outside of arcus tendineus 6, i.e., wrapping around arcus tendineus 6. This wrapped configuration places an implant material near the arcus tendineus, e.g., in surrounding tissue such as surrounding muscle tissue, which allows for ingrowth of tissue into the implant material located at path 14, and fixation of that implant material at that location. FIG. 2 illustrates an example of a circular tissue path, 14, that passes above arcus tendineus 6 near (e.g., within 2 centimeters, such as within 1 or 0.5 centimeters) ischial spine 8. Path 14 includes an arrow showing a direction of a needle (not shown) following path 14, starting below arcus tendineus 6, exiting the pelvic region by passing below the arcus tendineus and through the iliococcygeus muscle (levator ani) (not shown), passing around arcus tendineus 6, and then passing back into the pelvic region by passing above the arcus tendineus 6 through the obturator interims muscle (not shown).

FIG. 2 illustrates what can be referred to as a "bottom-up" technique for passage of an end portion or extension portion of implant material through a region of the arcus tendineus. The bottom-up method inserts a distal end of an extension portion of an implant below the arcus tendineus and through the iliococcygeus muscle; the implant extension portion distal end is then passed around the back or outside of the anus tendineus to a location above the arcus tendineus, and then through the tissue above the arcus tendineus (i.e., through the obturator internus muscle) where the implant end then re-enters the region of the pelvic floor.

Alternately, a tissue path as illustrated in FIG. 2 may be produced using a "top-down" method. As opposed to the bottom-up method specifically illustrated at FIG. 2, a top-down method inserts the implant extension portion distal end above the arcus tendineus through the obturator internus muscle, wraps the extension portion around the arcus tendineus, then the extension portion re-enters the region of the pelvic floor below the arcus tendineus by passing through the iliococcygeus muscle. A top-down method may be a preferred method because top-down methods allow a needle tip to extend away from the bladder when passing through the obturator internus muscle. In a top-down method, the implant extension distal end, after wrapping around the arcus tendineus and re-entering the pelvic floor region (i.e., through the iliococcygeus muscle), may be led through one of various tissue path options. For example, the end extension may re-enter the pelvic floor region and then extend to and terminate at a location internal to the pelvic region. The distal end of the extension portion could be sutured, e.g., using a "stay suture," to maintain placement within the pelvic floor. This method advantageously does not require an external incision for manipulating the extension portion. Another variation of the method is to use a tissue path as mentioned, but that continues through the pelvic region and then to and through an external incision such as through the buttock and then through an external incision, wherein the extension portion can be adjusted and cut off to a desired length.

Figure 3:
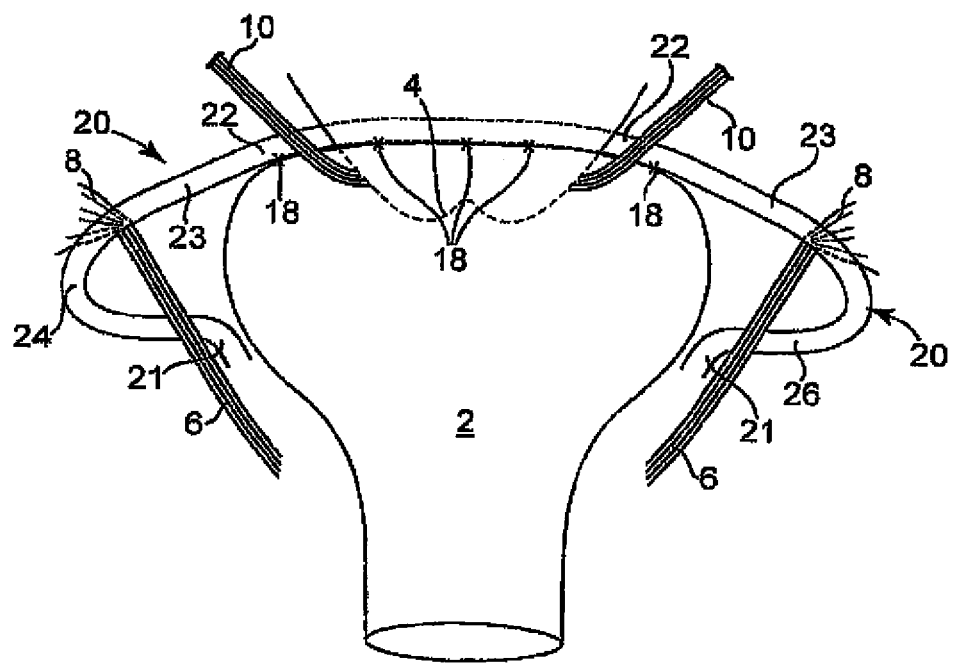
FIG. 3 illustrates anatomy relevant to the invention, including specific pelvic anatomy, and also exemplifies an implant according to the invention.

As illustrated in FIG. 3, embodiments of the invention involve the use of a single mesh bridge (e.g., a uniform mesh strip) implant between tissue paths described herein, above the white line and optionally and preferably near the ischial spines, to repair vaginal vault prolapse. Optionally, if desired, a mesh strip implant may use a modified middle section with denser construction (e.g., use of a biologic material for a middle section, 22) to hold sutures better than standard mesh. A vaginal vault repair results in an anatomically correct "pear" shape to the distal vagina, with the vaginal vault correctly positioned between the ischial spines.

Referring to FIG. 3, this figure illustrates a top view of the anatomy of FIG. 1 including a mesh support implant 20 installed according to an exemplary tissue path described herein. Implant 20 includes central (tissue support) portion 22 sutured to the apex of vagina 2 by sutures 18 (designated as "x"s). Implant 20 also includes two end portions, 24 and 26, extending bilaterally from tissue support portion 22. Each of end portions 24 and 26 is illustrated to pass from apex of vagina 2, laterally toward arcus tendineus 6. Each end portion 24 and 26 passes above arcus tendineus 6, near ischial spine 8—i.e., through tissue at the immediately anterior edge of ischial spine 8 and at the level of the ischial spine near the connection of the ischial spine to the arcus tendineus—through the obturator internus muscle (not shown), around arcus tendineus 6. In FIG. 3, extension portions 24 and 26 are shown to continue through tissue below the arcus tendineus (i.e., through the iliococcygeus muscle, not shown) and back into the pelvic floor region.

Referring still to FIG. 3, sections 21 and 23 of end portions 24 and 26 are located internal to the pelvic floor region. During a surgical implantation procedure, these portions can be manipulated by grasping manually or with a surgical instrument such as a forceps, needle-passer, or pliers, to adjust the position of end portions 24 and 26, as well as support portion 22 and overall implant 20.

The invention also relates to implants, tools, and kits, that may be used according to methods described herein, and that may also be useful for treating conditions other than vaginal prolapse, e.g., other types of pelvic tissue prolapse. In general, implants that may be useful according to methods described herein can include those types of implants known for use to treat vaginal prolapse, and similar implants. Exemplary implants can be in the form of a biocompatible mesh material such as a mesh strip made of a single uniform length of mesh, or, alternately, can be a multi-portion implant that includes a support portion for attachment to pelvic (e.g., vaginal) tissue connected to end portions or extensions. Embodiments include a length of mesh strip of generally uniform thickness and width, as well as implants having distinct or discernible sections of different sizes, materials, or mechanical properties. Other exemplary embodiments include a tissue support portion of a biologic material and extension portions of synthetic mesh material.

Exemplary implants may be a mesh strip such as mesh strips and multi-component implants illustrated in the accompanying figures. As illustrated, exemplary implants may consist of a strip of uniform thickness and width, as well as implants that include portions of different sizes, shapes, and materials, for connecting to tissue and for supporting tissue. A tissue support portion may be of a biologic material or a synthetic (e.g., mesh) material. Attached to a tissue support portion can be one, two, or more, extensions (or "extension portions" or "end portions") shaped and sized to extend from the point of attachment with the support portion of the implant to another location of the anatomy. Each extension may be an elongate material that is biologic or synthetic, e.g., an elongate synthetic mesh attached directly to the support portion.

Various implant products are available commercially for treating prolapse conditions, e.g., from American Medical Systems Inc., of Minnetonka Minn. Examples of such products include: the line of PERIGEE™ products for treatment of cystocele, from American Medical Systems, Inc.; the APOGEE™ product for treating enterocele, rectocele, and vaginal vault prolapse, also available from American Medical Systems Inc.; as well as products for CAPS procedures (combined-prolapse-repair-with sling) for treating cystocele and stress urinary incontinence.

Examples of implants that can be used or modified for use according to the present description are described, e.g., in US application number 2004/0039453, "Pelvic Health Implants and Methods," (describing implants useful for treating multiple pelvic disorders) having Ser. No. 10/423,662, and filed on Apr. 25, 2003; US application number 2005/0245787, "Method and Apparatus for Treating Pelvic Organ Prolapse," having Ser. No. 10/834,943, and filed on Apr. 30, 2004; U.S. patent application Ser. No. 11/347,063, filed Feb. 3, 2006, entitled "Pelvic Implants and Related Methods; U.S. patent application Ser. No. 11/398,368, filed Apr. 5, 2006, entitled "Articles, Devices, and Methods for Pelvic Surgery"; and U.S. patent application Ser. No. 11/243,802, filed Oct. 5, 2005, entitled "Method for Supporting Vaginal Cuff" the entireties of each of these being incorporated herein by reference.

Exemplary implants can include a tissue support portion for placing in contact with tissue to be supported, and one or more "extension" portions (or "end portions"), the tissue support portion being useful to support pelvic tissue such as vaginal tissue (anterior, posterior, apical, etc). The tissue support portion can be sized and shaped to contact the desired tissue when installed. A tissue support portion that is located between two or more extension or end portions is sometimes referred to herein as a "central support portion."

Dimensions of an implant or a portion of an implant can be as desired and useful for any particular installation procedure, treatment, or combination of treatments, and to support a specific tissue, type of tissue, or multiple tissues (e.g., bladder, vagina, urethra, etc.). Exemplary dimensions can be sufficient to allow the tissue support portion to contact tissue to be supported and to allow one or more extension portion to extend from the tissue support portion to a desired anatomical location, e.g., through a tissue path through a region of the arcus tendineus, as described.

A tissue support portion can be sized and shaped to an overall area for contacting tissue being supported, and can depend on the condition being treated, e.g., vault prolapse, enterocele, rectocele, or a combination of these. The tissue support portion is of sufficient size and shape to at least partially surround or otherwise be in contact to support prolapsed tissue. A tissue support portion can optionally be of a width that is greater than a width of an extension portion. An increased width of a tissue support portion may take the form of one or two lateral extensions that extend the width of the tissue support portion in at least one direction, beyond the width of an extension portion. The shape of the tissue support portion can also be varied, depending on the intended application and treated condition, and may be square, rounded, angled, rectangular, etc. Exemplary widths of a tissue support portion, measured laterally (i.e., perpendicular to lengths of extension portions), can be in the range from 1 to 8 centimeters, such as from 2 to 6 centimeters. Generally, exemplary lengths of a tissue support portion can be up to 8 centimeters, such up to about 4 centimeters.

Extension portions are elongate pieces of material that extend from the tissue support portion and are integral with or connected to the tissue support portion. Extension portions are useful to attach to other anatomical features and thereby provide support for the tissue support portion and the supported tissue. One or multiple (e.g., one, two, or four) extension portions can extend from the tissue support portion as elongate "ends," "arms," or "extensions," that are used to attach to other anatomy. Extension portions extending from a tissue support portion in contact with posterior vaginal tissue, can be extended through a tissue path as described herein, passing through a region of the arcus tendineus such as above the arcus tendineus.

A width of an extension portion can be a width useful for implanting the implant and for providing desired strength and fixation properties during and after implantation and optional tensioning of the sling. Typical widths of an extension portion can be in the range from 0.5 to 3 centimeters, e.g., from 0.8 to 2 centimeters, such as from 0.8 to 1.5 centimeters. Extension portions can typically have a uniform or substantially uniform width along the length, normally not varying by more than about 25 percent of the average width along the length of the installed portion of the extension portion. A length of an extension portion can be as desired to extend from a tissue support portion installed at a desired pelvic tissue location, through a tissue path of a desired length, e.g., from a tissue support portion installed at a vaginal tissue, to a region above the arcus tendineus, optionally back into the pelvic cavity, and optionally further passing through the buttock to an exterior incision external to the buttock.

An example of a particular type of pelvic implant is the type that includes supportive portions including or consisting of a central support portion and two elongate extension portions extending from the central support portion. The term "supportive portions" refers to portions of an implant that function to support tissue after the implant has been implanted, and specifically includes extension portions and a tissue support portion, and does not include optional or appurtenant features of an implant such as a sheath, dilator, attached or engaged insertion tool, or other connected tools or implantation aids. FIGS. 4, 5, and 6, for example, illustrate implants having supportive portions consisting of a tissue support portion and two elongate extension portions.

According to certain embodiments of implants, various features can be incorporated into a useful implant to facilitate installation of a device during a surgical procedure. For instance, a suture may be attached to an implant, along a length of an extension portion, for use in adding tension or in positioning the implant or a portion (e.g., extension) of the implant. Alternately or in addition an exemplary implant may include a removable sheath such as a flexible plastic, transparent elongate tube that can cover extension portions of an implant to allow a surgeon to apply tension or pressure on the sheath to indirectly apply pressure or tension to the extension portion, for placing or adjusting the location of the implant.

An implant can be installed according to the present description by use of standard surgical instruments, or by use of instruments that are designed or particularly useful for placing an extension portion through a tissue path as described, e.g., in a region of the arcus tendineus, such as above the arcus tendineus. Generally, an insertion tool may include a portion for creating a tissue path, that portion being curved or straight, with exemplary embodiments including a curved portion of a sized and shaped (e.g., length and curvature) that will be useful to form a tissue path as described herein, in a region of the arcus tendineus and preferably wrapping around the arcus tendineus, to lead a distal end of an extension portion at least partially through a tissue path that wraps around the arcus tendineus. An exemplary length (measured as the circumferential arclength of the curved portion) of a curved portion can be from 3 to 5 centimeters, and an exemplary radius of curvature of a curved portion may be, e.g., in the range from 0.5 to 1.5 centimeters.

Exemplary geometric forms of a curved portion can be a form of a partial circle, such as a half circle. The partial circle is arranged to be in a plane that does not include a line defined by a longitudinal axis of a shaft. With this configuration, the curved portion can be located to define a partial circle having the shaft of the tool (and a longitudinal axis of the shaft) as a center of the circle. The curved portion can then engage tissue and be rotated around the shaft and longitudinal axis by rotation of the handle about the longitudinal axis, to cause the curved portion to define a circular tissue path. The partial circle can have a relatively uniform radius of curvature, such in the range from 0.5 to 1.5 centimeters (e.g., from 0.7 to 1.2 centimeters), extending over an arclength that traverses from 90 to 270 degrees, e.g., from 170 to 190 degrees, about 180 degrees. This arclength, when measured as the circumference of the partial circle, can be, e.g., from 3 to 5 centimeters.

An example of a useful insertion tool is a small curved needle attached at a distal end of an extension portion, which can be manipulated using a surgical instrument such as a forceps or pliers. The small curved needle can consist of a single length of curved needle material, e.g., metal or plastic, attached at a distal end of the extension portion. The needle may be considered to be a two-dimensional form, in that it the curvature of the needle can define a two-dimensional plane. The small curved needle may be manipulated transvaginally and passed through tissue in a region of the arcus tendineus, preferably near the ischial spine. The needle is curved to exit the pelvic region, wrap around the ischial spine, and then lead the extension portion back into the pelvic region to cause the extension portion to follow a tissue path that wraps around the arcus tendineus. The needle may then be removed by cutting the extension portion and the position of the extension portion may be adjusted by manipulation of portions of the extension portions that are located within the region of the pelvic floor.

Another example of a tool useful for placing an end portion of an implant transvaginally is a small three-dimensional looped needle such as a Deschamps needle or a similar needle that can be introduced transvaginally and that can then be used to pass an end portion of an implant through a tissue path in a region of the arcus tendineus, e.g., at the level of the ischial spine. The tool can be considered to include a shaft and curved end portion that exist in three dimensions, with the shaft defining a longitudinal axis and the curved end portion originating from that axis and extending in two additional directions. In use, an end portion of an implant may be attached to a tip of a curved distal portion of the tool and passed through tissue of a region of the arcus tendineus using the curved tip, transvaginally. For example, the curved distal end portion can be inserted transvaginally, and the handle can be rotated to rotate the curved distal end portion to define a circular tissue path. The needle is curved to exit the pelvic region, wrap around the arcus tendineus, and then lead the extension portion back into the pelvic region to cause the extension portion to follow a tissue path that wraps around the arcus tendineus. Optionally, according to certain exemplary methods, an additional surgical tool such as a tunneler (e.g., the IVS Tunneler device available commercially from Tyco) can be inserted through an external incision (e.g., in a peri-rectal region) into the pelvic region, attached to a distal end of the extension portion, and then removed to lead the extension portion of the implant from the pelvic region to an external location.

An insertion tool or tools (e.g., Deschamps needle, or a small needle to be manipulated by a standard operating room tool such as a needle-driver) may engage a distal end of an extension portion of an implant by any useful engagement configuration. The engagement may be a permanent attachment or removable engagement, as desired.

According to certain embodiments of the invention, an insertion tool may be attached to the implant at a distal end of an extension portion. The term "attach," when used with regard to an end portion attached to an insertion tool, will refer to engagement configurations that are not easily removable, such as in an a manner designed to be used during a surgical implantation method and that would normally be removed only by cutting the extension portion of the implant, as opposed to releasing (e.g., un-threading) the implant from the insertion tool. Examples of types of attachment mechanisms include attachment by adhesive such as a pressure sensitive adhesive, a structural adhesive, a two-part reactive adhesive such as an epoxy adhesive, etc.; a tight knot using thread or suture material that would not be easily untied during a surgical installation procedure; a non-removable mechanical interaction between the insertion tool and the implant portion such as by permanently threading the implant portion through an eye, eyelet, slot, or hole in the tool so the end portion is not easily removed; a metal or plastic mechanical attachment such as a metal crimp at the end of the insertion tool; a polymeric attachment such as the use of a heat-shrinkable polymeric sheath; attachment by a molding manufacturing process such as by injection molding or insert molding a plastic dilator or plastic needle to a distal end of an extension portion; or any other mechanical or adhesive type of permanent or semi-permanent attaching mechanism. In contrast to an attachment, examples of types of removable engagement mechanisms include use of a loose knot that is easily untied during a surgical implantation procedure; an threaded dilator that removably engages a threaded needle tip for easy engagement and dis-engagement by threading and un-threading; and threading a distal end of an extension portion through an aperture (e.g., eye or eyelet) of an insertion tool such as a needle or a curved distal portion of a tool.

Attaching an insertion tool (e.g., dilator, needle, etc.) to a distal end of an extension portion of an implant eliminates the need for a surgeon to make that connection, which reduces preparation of the implant before or during surgery. The term "pre-attached" refers to an implant that includes an insertion tool attached to the implant as the implant is commercially supplied to a surgeon. The pre-attached device can be manufactured for distribution and sale in a condition where only minimal preparation (if any at all) needs to be performed by the surgeon prior to surgical implantation. Minimal preparation may include modification to size or shape of a portion of an implant (e.g., by trimming), or removing loose material or loose pieces, but does not include a step of creating a direct attachment between a portion of the implant and an insertion tool that will allow the portion of the implant to be placed or led through a tissue path.

Thus, embodiments of optional features of implants include an insertion tool that is attached e.g., pre-attached, or alternately is removably engaged, at a far (i.e., distal) end of an extension portion of an implant, the tool being a structure that facilitates installation of the extension portion and implant by being of a size, shape, rigidity, and overall design, to be capable of being used transvaginally to create a tissue path that passes through tissue in a region of the arcus tendineus, optionally and preferably wrapping around the arcus tendineus. Examples of insertion tools that may be either attached or removably engaged to a distal end of an extension portion include: a tip (distal end) of an extension portion that includes an attached rigid tip or "dilator," optionally designed to cooperate and removably engage an end of another insertion tool for use together to create a tissue path during installation of an implant; a distal end of an extension portion that is permanently attached to an insertion tool in the form of a curved distal needle portion and a shaft and proximal handle portion, or another tool that can be inserted transvaginally to manipulate an extension portion of an implant during installation; and a distal end of an extension portion that is permanently attached to an insertion tool such as a small needle that can be manipulated by a grasping tool such as a needle driver, a forceps, or a pliers, etc., to manipulate an extension portion of an implant during transvaginal installation.

As one exemplary design, an implant may include a rigid (e.g., plastic), pushable dilator attached at a distal end of an extension portion, the dilator including a sharp tip at a first end and an opening at an opposing end, the opening designed and adapted to fit and removably engage an end of an insertion tool such as a needle. The pushable dilator can be designed to fit the leading edge of an insertion tool such as a long needle having a handle and a distal portion with a tip adapted to fit and removably engage the pushable dilator. The dilator can engage the end of the insertion tool and may be pushed or pulled by the insertion tool through tissue to either follow or produce a path in the tissue, such as by rotating the handle to cause the distal portion to produce a curved tissue path. To produce a path in the tissue by pushing the dilator through the tissue, the pushable dilator can be sufficiently sharp and rigid to pass through tissue when pushed using the needle (e.g., by rotating the needle).

A dilator (whether or not sufficiently sharp and rigid to be "pushable") may be straight, or, according to certain specific embodiments of the invention, may be curved in a manner that will improve manipulation of the dilator during a surgical procedure, e.g., in a manner that will facilitate pushing the dilator through tissue to either produce or follow a particular path of tissue. Optionally for use with methods described herein with a tissue path in the region of the arcus tendineus, e.g., that wraps around the arcus tendineus, the external size and shape of a dilator may be suited to produce a tissue path that curves around the arcus tendineus, e.g., to exit the pelvic region by passing through the obturator internus above the arcus tendineus, pass behind the arcus tendineus, and re-enter the pelvic region by passing through the levator ani at a location below the arcus tendineus. The curved dilator may be considered to be a two-dimensional form, in that it the curvature of the dilator can define a two-dimensional plane.

As exemplary dimensions, a curved dilator may include a curved portion that has a radius of curvature in the range from 0.5 to 1.5 centimeters and a length (measured as the arclength of the curved portion) of from 3 to 5 centimeters. Also optionally, a curved shape or radius of a curved dilator can approximate or match a curved shape or radius of an insertion tool (e.g., a curved distal portion of an insertion tool such as a curved distal needle), and the curves of both a dilator and a curved distal portion of an insertion tool (e.g., needle) may be shaped to mach a tissue path that exits the pelvic area at a location near the ischial spine and above the arcus tendineus by passing through the obturator internus muscle, continues around the arcus tendineus, and re-enters the pelvic region below the arcus tendineus by passing through the levator ani muscle. Thus, according to certain specific embodiments of the use of a curved dilator, a curved dilator may be used with a curved needle (or other insertion tool) designed to fit within an internal space at a hollow interior of the dilator, with the curved insertion tool and the curved dilator having a size and shape to define a tissue path passing around the arcus tendineus as described.

Further design features can relate to dilators and insertion tools that include anti-rotation or alignment features, in particular with the use of a curved needle insertion tool and a curved dilator. An anti-rotation or alignment feature may be in the form of opposing and coordinated structural features of the dilator and a tip of an insertion tool (e.g., needle) that together can: interconnect the dilator and tip of insertion tool to produce a desired alignment; prevent relative movement of the two pieces such as to prevent rotation of the dilator relative to the tool; or both. The alignment feature causes the dilator to be placed on the needle in a specific alignment, which if the needle and dilator are both curved as discussed above, causes the curve of the needle to be aligned with the curve of the dilator. An example of an alignment and anti-rotation feature is a keyed structure, as will be understood, that includes one or more inter-connecting surfaces and structures between the dilator and the needle to allow the dilator to removably connect to the needle when the two are properly aligned, and then to also prevent rotation between the two when the two are connected. Other mechanical structures will also allow the dilator to be attached at an end of a needle in a manner to produce a desired alignment and to prevent rotation of the dilator relative to the needle.

An example of an implant having a curved (two dimensional) dilator adapted to removably engage a three dimensional insertion tool that includes a curved (two dimensionally curved) distal end, is illustrated at FIG. 4. FIG. 4 schematically illustrates a prolapse support device (i.e., implant) 110 for treating vaginal prolapse, and insertion tool 122. Implant 110 includes end (i.e., "extension") portions 114 and 116 connected to central support portion 120. Sutures (optional) 118 extend along the lengths of each of extensions 114 and 116 and are connected to central support portion 118 and extensions 114 and 116. Rigid, curved dilators (in two dimensions) 112 are attached at each distal end of extension portions 114 and 116.

Still referring to FIG. 4, insertion tool 122 (not to scale) includes handle 124, shaft 126, and curved distal portion or "needle" 128. (Needle 128 includes a two-dimensional semi-circular form, and needle 128 along with shaft 126 together are in three dimensions.) Needle 128 is designed to engage dilators 112 by fitting inside of a dilator 112, e.g., inside of internal space 113 of each dilator, so that needle 128, by use of handle 124 of tool 122, can be used to push dilator 112 through tissue by rotating handle 124; rotation of handle 124 about axis 121, defined by handle 124 and shaft 126, rotates curved needle 128. Curved needle 128, shaft 126, and handle 124 are in three dimensions. Curved needle 128 is substantially a partial circle (e.g., half circle) that rotates to define a curved tissue path when handle 124 is rotated about longitudinal axis 121. Not shown is an optional protective flexible cover or sheaths that could extend over and contain extension portions 114 and 116.

Figure 4A:
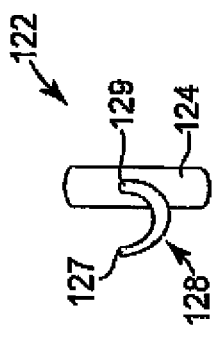
FIG. 4A is an end view of an exemplary tool.
Figure 4B:
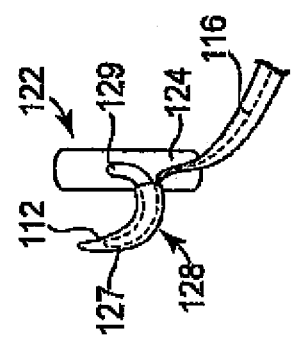
FIG. 4B is an end view of an exemplary tool with attached dilator of an implant.

FIG. 4A shows an end view of tool 122, illustrating the half-circle shape of curved end 128, in view of handle 124. Curved end 128 includes an arclength of approximately 180 degrees, starting at a trailing end 129 that connects to shaft 126, and extending to needle tip 127. FIG. 4B illustrates these features of tool 122 when connected to dilator 112, which is also attached to extension portion 116 of implant 110.

According to other embodiments of implants, distal ends of extension portions can be attached or engaged with an insertion tool in the form of a needle or in the form a tool comprising a distal curved portion (e.g., needle) with attached shaft and handle, the former needle being capable of being manipulated using a separate tool such as a needle-driver, forceps, or surgical pliers, the latter type of needle being capable of being manipulated using the handle, which will be external to the patient during a transvaginal surgical procedure. Thus, exemplary insertion tools include a small two-dimensional needle that can be manipulated during a transvaginal installation by another surgical tool; a tool having a distal portion comprising a curved needle (including a needle tip), shaft, and handle, that can be used directly to install the implant; a dilator; or another type of tool that can be used to allow ends of an extension portion of an implant to be transvaginally installed in tissue as desired.

A specific example of an attached insertion tool can be a small needle that can be securely attached at distal end of an extension portion of an implant. The needle can be straight or curved (e.g., in two dimensions), and may preferably be sized to be manipulated using a standard surgical grasping instrument such as a pliers, forceps, or needle-passer, and can be can be shaped and sized as desired, such as with a curve and length that facilitate passing the needle through a tissue path that wraps around an arcus tendineus. For example, pre-attached small, two-dimensional curved needle may include a curved portion that has a radius of curvature in the range from 0.5 to 1.5 centimeters and a length (measured as the arclength of the curved portion) of from 3 to 5 centimeters. A distal end of an extension portion of an implant may be attached at a trailing end of the needle. (Attachment at trailing end of a needle or at a leading end of a needle refers to attachment that is within a distance of an end of a needle of 25 percent of the total needle length.) The attached insertion tool (e.g., needle) can optionally include useful features that allow manipulation and placement of the needle as desired to place the implant in a useful position. For example, a needle may include flat portions that allow easy grasping and manipulation with a standard needle-driver, forceps, or pliers. The needle may be plastic or metal. The curve and sizing of the needle can be shaped to match a tissue path that exits the pelvic area at a region of the arcus tendineus, wraps around an arcus tendineus, and re-enters the pelvic region.

FIG. 5 schematically illustrates a prolapse support device for treating vaginal prolapse, the device including attached insertion tools in the form of small curved two-dimensional needles having length L and radius of curvature R. Implant 130 includes end portions 134 and 136 connected to central support portion 140. Sutures 138 extend along the lengths of each of extensions 134 and 136 and are connected to central support portion 140 and extensions 134 and 136. Attached insertion tools 132, in the form of small curved two-dimensional needles, are attached to distal ends of extensions 134 and 136. Length L (the arclength of each needle) can be as desired, e.g., from 3 to 5 centimeters. Curvature of radius R can be as desired, e.g., from 0.5 to 1.5 centimeters. Insertion tools 132 are designed to be transvaginally manipulated by a tool such as a needle driver, surgical pliers, surgical forceps, etc., during installation of implant 130, e.g., according to methods described herein.

FIG. 6 schematically illustrates a prolapse support device that includes an implant having two pre-attached insertion tools. Implant 142 includes end portions 144 and 148 connected to central support portion 150. Sutures 146 extend along the lengths of each of extension 144 and 148 and are connected to central support portion 150 and extensions 144 and 148. Insertion tools 152 include shaft 156, handle 154, and curved distal portion, needles 158, each needle being attached at a distal end of extension portions 144 and 148.

Figure 9:
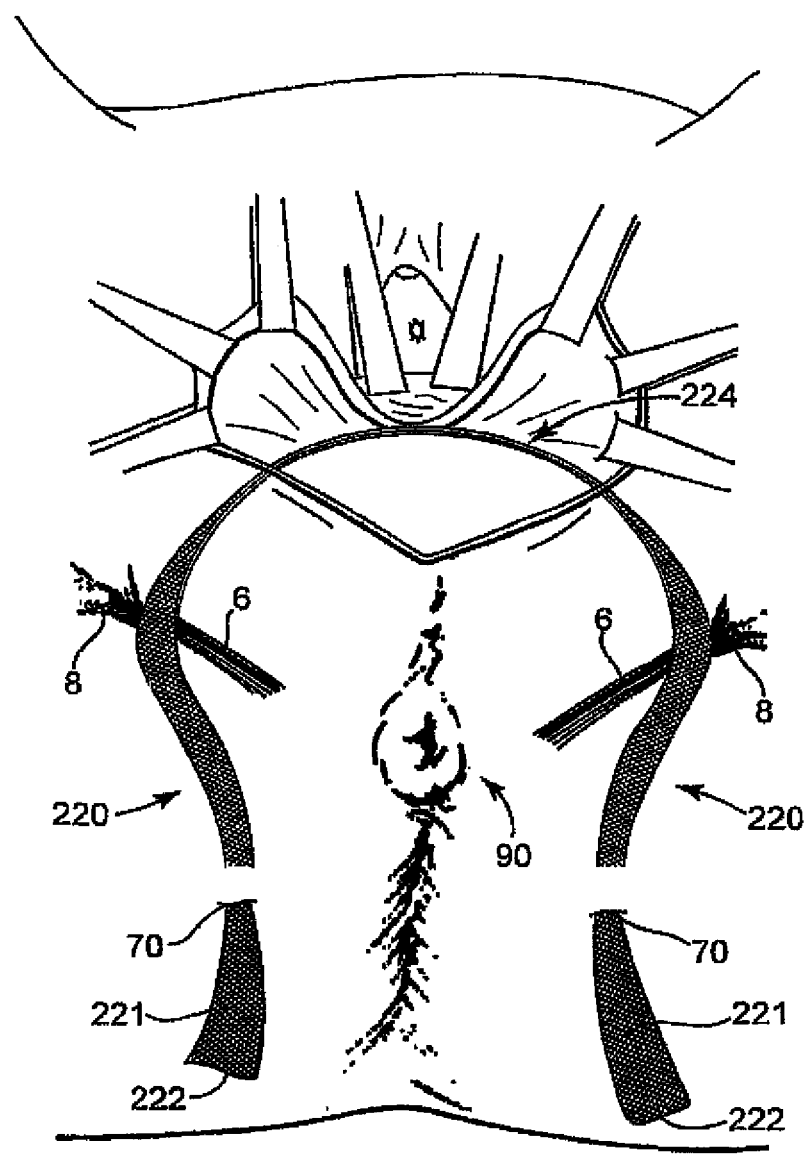
FIG. 9 illustrates an exemplary implanted pelvic implant according to the invention.

Each tool 152 includes handle 154, shaft 152, curved needle end 158 at a distal end of shaft 152, and needle tip 160. Tips 160 are leading edges of curved needles 158, and each is attached to a distal end of an extension portion 144 or 148. With this design, a surgeon receives the implant product 142 with tools 152 attached; the surgeon installs implant 142, transvaginally, with support portion 150 being attached to vaginal tissue. The surgeon uses each of tools 152 to place ends of extension portions 146 and 148 bilaterally through tissue in the region of the arcus tendineus, e.g., near the ischial spine. Curved distal end 158 of each tool 152 allows the surgeon to lead a distal end of each extension portion 144 and 148 around the outside of the arcus tendineus and back into the pelvic region at a location below the arcus tendineus, e.g., through the iliococcygeous muscle. This placement can be performed by movement or each tool 152, the movement including rotation of handle 154 about an axis that includes shaft 156, to rotate curved distal end 158, also about the axis of shaft 156. This can pass tip 160 and a distal end of an extension portion around an arcus tendineus, with the distal end exiting and re-entering the pelvic region. The surgeon can then disconnect the end of each extension portion from each tip 160 by cutting the extension portions 144 and 148 near tip 160 of each tool 152. After cutting the end of each extension portion 144 and 148, the needle and tool can be removed from the pelvic region and each extension portion 144 and 148 can be manipulated to adjust and position the extension portion and implant 142 as desired to support vaginal tissue connected to support portion 150. This can optionally include producing another tissue path to an external location and leading the end of each extension portion 144 and 148 through that tissue path to the external location in the perirectal region such as is illustrated in FIGS. 7 and 9. Or, each extension portion 144 and 148 can be severed and severed ends can be left at locations within the pelvic floor region without leading extension portions 144 and 148 to an external incision.

Figure 10:
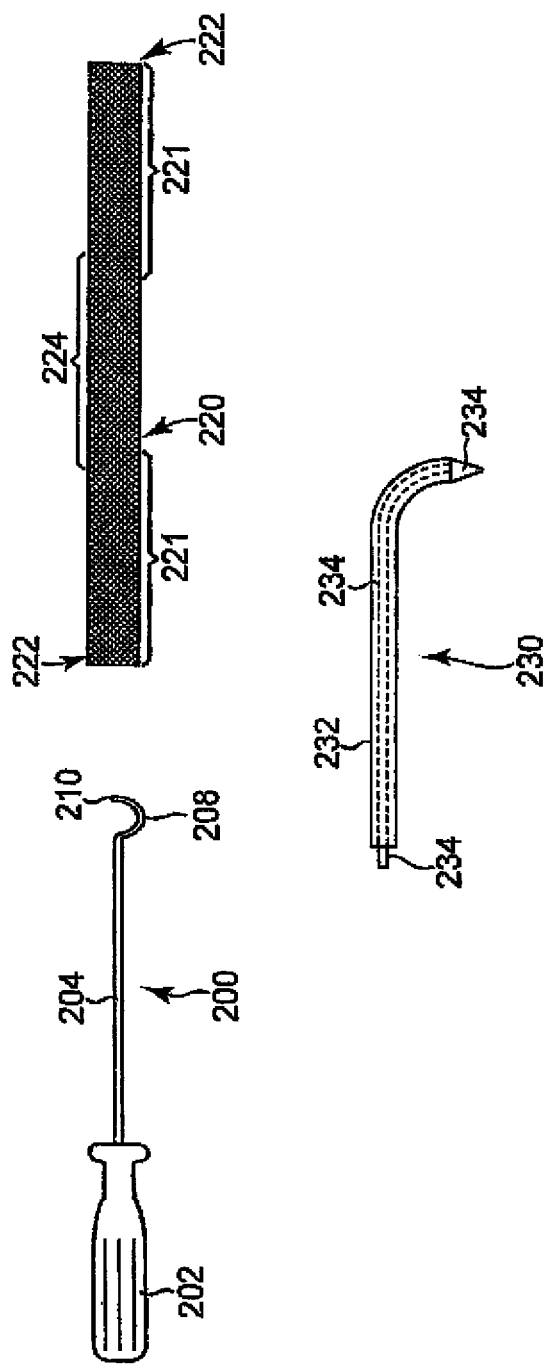
FIG. 10 illustrates an exemplary kit or system according to the invention, including a Desehampes Needle, an implant, and a tunneler device.

According to particular embodiments, a kit according to the invention can include an implant and a tool or multiple tools for installation, e.g., with the insertion tool being either removably enjoyable or attached (e.g., permanently) at a distal end of an extension portion of the implant. Referring to FIG. 10, a kit is illustrated (not to scale) to include a mesh tape implant (220) for supporting vaginal tissue, insertion tool 200 comprising a distal end having a curved needle, and tunneler device 230. FIG. 4 includes an illustration of an exemplary insertion tool useful for installing a mesh to pass above the arcus tendineus. Tool 200 (Deschamps Needle) of FIG. 10 is shown as a side view. Tunneler device 230 (e.g., IVS tunneler) includes hollow trocar 232 and flexible plastic plug 234, as are known. Tool 200 includes handle 202, shaft 204 having a proximal end connected to handle 202, shaft 204 connected at a distal end to curved end (e.g., "needle") 208. The diameter of the curved needle portion 208 is shown to be 1 inch, meaning that the radius of curvature is about 0.5 inch; other sizes of the curve may also be useful. Curved end 208 defines a two-dimensional curve, and the combination of curved end 208 with shaft 204 together are in three dimensions.

Still referring to FIG. 10, tip 210 of curved end 208 can be adapted to allow an end of a mesh implant to be held (removably engaged) by tip 210. Tip 210 can also be sharpened to allow the tip to be passed through tissue. Tool 200 may be a Deschamps Needle or similar structure having a handle, shaft, and a curved portion at the end of the shaft. A distal end (222) of mesh implant 220 can be attached to the end. (tip) of curved portion of curved needle 208 of tool 200. During use, a surgeon can make a vaginal incision to allow transvaginal insertion of curved end 208 of tool 200, with a distal end 222 of implant 220 attached at the end (tip) 210 of curved portion 208. Center portion 224 of implant 220 is attached to the vaginal apex to provide support, and each of ends 222 can be extended bi-laterally through tissue paths that pass through a region of the arcus tendineus, such as through the obturator internus muscle just above the arcus tendineus at the level of the ischial spine. Tunneler device 230 can be used to separately retrieve each of ends 222 of mesh implant 220 and draw ends 222 through a tissue path to an external incision, e.g., an external incision in the perirectal region.

The invention contemplates placement of an implant, as described, to treat a condition of vaginal tissue prolapse, by use of transvaginal surgical methods. The present description identifies certain combinations of implants, tools, and procedures, but as will be understood based on the present description, many different variations on the present methods, tools, and procedures will be useful, as will combination of implant, tool, and procedure.

According to one embodiment of the invention, using a curved Deschamps or similar needle, an extension portion of an implant can be inserted trough a vaginal incision and a central portion of the implant can be attached to vaginal tissue that is to be supported. Two opposing tissue paths are created from the vaginal tissue to regions of the arcus tendineus, e.g., above the arcus tendineus at a level of the ischial spine, one on each side of the pelvic region. Each end ("extension") portion of the implant can then be extended through a tissue path and above or below the arcus tendineus, such as through the obturator internus muscle or iliococcygeus, optionally also as close to the ischial spine as possible, using the curved needle. The end portion of the implant is passed around the outside of the white line and passed back into the pelvic region either below or above the white line, either through obturator internus or the iliococcygeus muscle. This location of the mesh end is illustrated in FIGS. 7, 7A, 8, 9, and 9A. The end of the mesh thus passes back into the pelvic floor and can be subsequently passed through a tissue passage that is created below that pelvic floor location, to an incision made external to the rectal region at each buttock (e.g., 2 to 3 centimeters lateral and 2 to 3 centimeters posterior to the anus).

Methods of the invention can involve placement of an implant and extension portion using a system as shown in FIG. 4. Distal curved portion 128 of tool 122 is engaged with interior space 113 of dilator 112, and tool 122 can be inserted transvaginally and rotated to produce a tissue path in a region of the arcus tendineus. Tool 122 then engages the second dilator to make a second opposite tissue path, transvaginally. Each extension portion can be adjusted as desired, and tissue support portion 120 can be attached to vaginal tissue and adjusted. In alternate embodiments that also use tool 122 and implant 110, a tissue path can be produced transvaginally using tool 122, as a first step, then dilator 112 can be engaged with distal end 128 after formation of the tissue path. After engaging dilator 112 and distal end 128, tool 122 can be counter-rotated to cause the dilator to be pulled back through the tissue path. The extension portion and tissue support portion 120 can then be adjusted.

Methods of the invention include variations that advantageously do not require any external incision such as two incisions perirectal incisions. Again entering the pelvic region transvaginally, e.g., using a curved Deschamps Needle (or alternately a small curved needle as shown in FIG. 5), an extension portion of an implant can be inserted through a vaginal incision and a central portion of the implant attached to vaginal tissue that is to be supported. Opposing tissue paths are created starting at the vaginal tissue and extending to opposite locations at regions of the arcus tendineus, e.g., above the arcus tendineus at the level of the ischial spine. Each end portion of the implant can then be extended through one of the opposing tissue paths and through obturator internus muscle, as close to the ischial spine as possible. The end portion of the implant is passed (wrapped) around the outside of the white line and passed back into the pelvic region below the white line, through the iliococcygeus muscle. The end of the mesh thus passes back into the pelvic floor. Instead of passing the end portion through a tissue passage that is created between that pelvic floor location and an external incision (e.g., in the rectal region at each buttocks), however, the end portion can be cut off, e.g., within the pelvic region, and the severed end left in that internal position of the anatomy. The end portion may optionally be secured using a suture. The severed end portions of the implant will remain in place within the defined tissue path and will the implant will support the vaginal tissue.

FIG. 7 illustrates an installed mesh tape implant 220 (e.g., as shown in FIG. 10) that includes a central support portion (224) secured to tissue of the vaginal apex. Each of two distal ends 222 of extension portions 221 of implant 220 extends bilaterally to pass above each arcus tendineus (6), near each ischial spine (8). Each of the two distal ends 222 of extension portions 221 of implant 220 then passes thorough the iliococcygeus muscle (not shown), below the white line (6), back to the pelvic floor region and then through two tissue paths, each path extending to an external incision (70) in the perirectal region.

FIG. 7A illustrates an alternate embodiment of an installed mesh tape implant 220 (e.g., as shown in FIG. 10) that includes a central support portion 224 secured to tissue of the vaginal apex. Each of two extension portions 221 of implant 220 extends bilaterally to pass above each arcus tendineus (6) near each ischial spine (8). Each of the two extension portions 221 of implant 220 then passes thorough the iliococcygeus muscle (not shown) below the white line (6) and back to the pelvic floor region. Each of the two extension portions 221 of implant 220 is severed to create an end of the extension portion located within the pelvic floor and extension portions 221 are not extended through tissue paths to any external incision.

Figure 8:
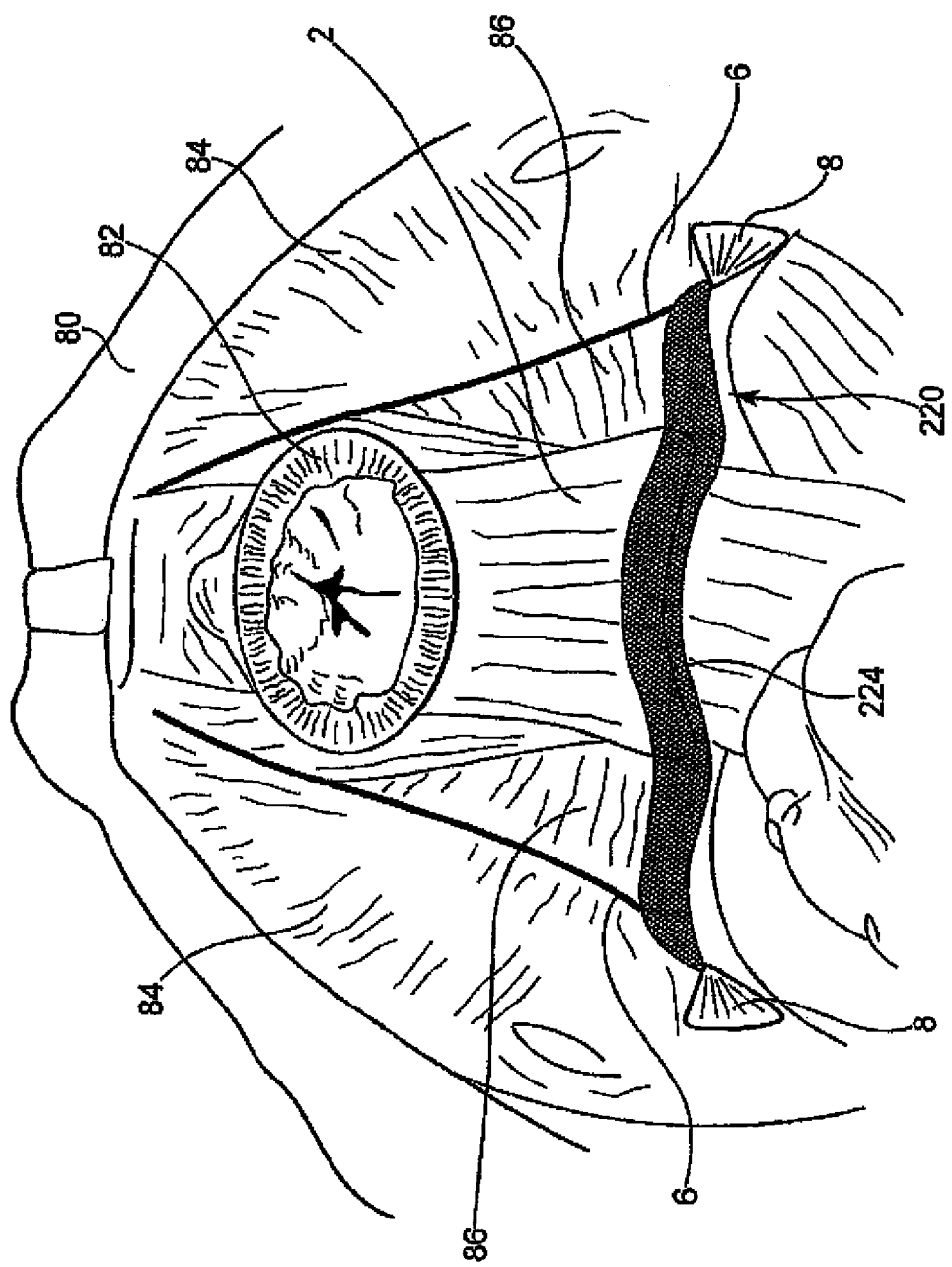
FIG. 8 illustrates an exemplary implanted pelvic implant according to the invention.

FIG. 8 illustrates another view of an installed mesh tape implant, such as implant 220 shown in FIG. 10. FIG. 8 looks in a direction down into the pelvic cavity, such as from a position in the abdomen. For reference are shown pubic bone 80, bladder 82, obturator internus muscle 84, and iliococcygeous muscle 86. In FIG. 8, a central support portion 224 of a mesh implant 220 is secured using sutures (not shown) to tissue of the apex of vagina 2. Each of the two distal ends 222 of extension portions 221 of implant 220 are extended bilaterally and passed through opposing tissue paths above each arcus tendineus (6), near each ischial spine (8), e.g., through obturator internus muscle 84. The far portions and distal ends 222 of the extension portions 221 of implant 220 are not shown in FIG. 8. These far portions of extension portions 221 may extend through alternate tissue paths, such as back into the pelvic region by passing through iliococcygeous muscle 86 at a location below arcus tendineus 6, then either severed at a location within the pelvic floor region or passed to an external incision.

FIG. 9 illustrates still another view of an exemplary installed mesh tape implant 220 that includes central support portion 224 secured to tissue of the vaginal apex. FIG. 9 is a view from exterior of the patient, facing the vagina and anus (90). Each of two distal ends 221 of the implant 220 extends bilaterally to pass above each arcus tendineus 6 near each ischial spine 8, around the arcus tendineus 6, and then thorough the iliococcygeus muscle (not shown) below the white line 6 and back to the pelvic floor region. From there each extension portion 221 passes through a tissue path extending to an external incision (70) in the perirectal region.

Figure 9A:
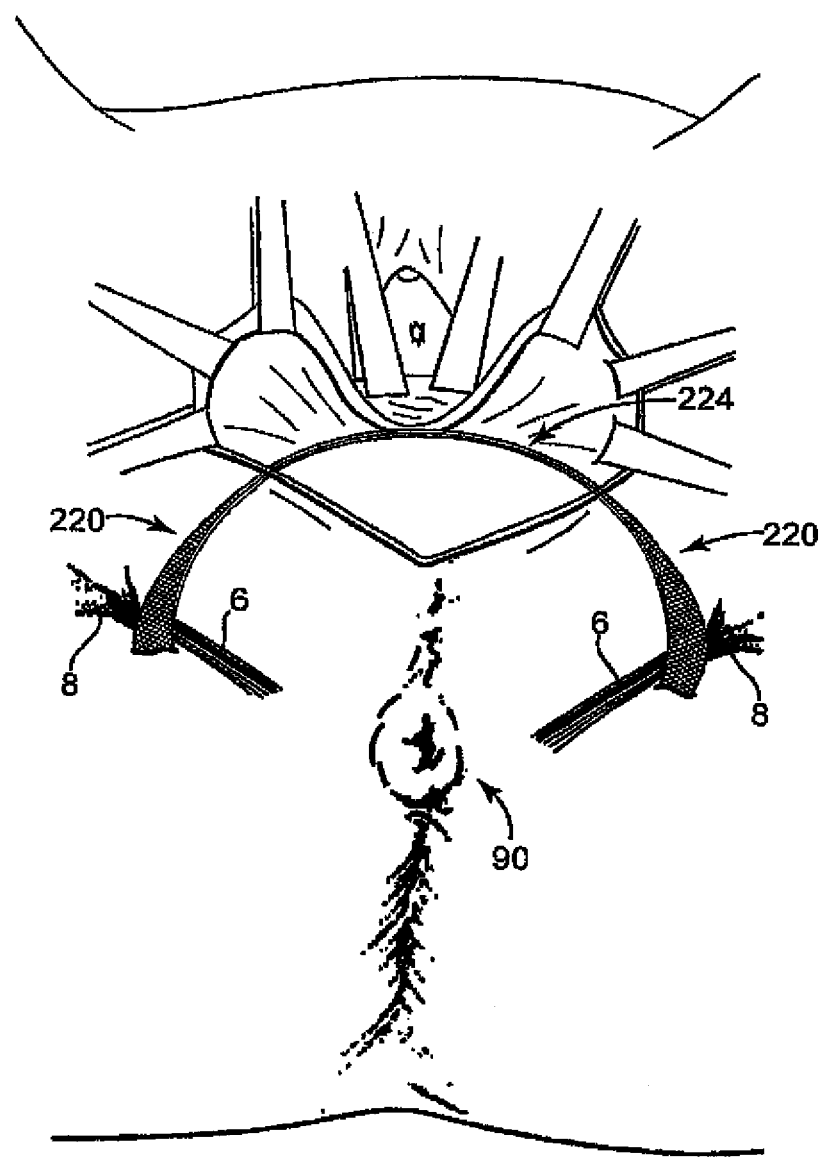
FIG. 9A illustrates an exemplary implanted pelvic implant according to the invention.

FIG. 9A illustrates an alternate embodiment of an installed mesh tape implant that includes a central support portion 224 secured to tissue of the vaginal apex. FIG. 9 is a view from exterior of the patient, facing the vagina and anus (90). Each of two extension portions 221 of implant 220 extends bilaterally to pass above each arcus tendineus 6 near each ischial spine 8. Each of the two extension portions 221 of the implant 220 then passes around arcus tendineus 6 and then through the iliococcygeus muscle (not shown) below the white line 6 back to the pelvic floor region. Each of the two ends of the implant is severed to create an end that remains internally within the pelvic floor, and the end portions are not extended through tissue paths to external incisions in the perirectal region.

The invention claimed is:

1. A method of supporting posterior vaginal tissue, the method comprising:
   providing an implant comprising a tissue support portion and an extension portion extending from the tissue support portion,
   creating an incision,
   contacting the support portion with posterior vaginal tissue,
   producing a tissue path that passes between a position of the tissue support portion and a region of an arcus tendineus, wherein the region of the arcus tendineus comprises a region from 2 centimeters above the arcus tendineus to 2 centimeters below the arcus tendineus and between an ischial spine and a distance 3 centimeters anterior to the ischial spine,
   wherein the tissue path passes below the arcus tendineus through an iliococcygeus muscle, wraps around the arcus tendineus to a location above the arcus tendineus, through an obturator internus muscle, and back to a region of the pelvic floor, and
   extending the extension portion through the tissue path.

2. The method of claim 1, comprising treating a condition selected from the group consisting of enterocele, rectocele, apical prolapse, and vault prolapse.

3. The method of claim 1, wherein the region of the arcus tendineus further includes the region between the arcus tendineus and 1 centimeter above the arcus tendineus, and between the ischial spine and a distance 1 centimeter anterior to the ischial spine.

4. The method of claim 1, wherein a distal end of the extension portion is sutured to the pelvic floor.

5. The method of claim 1, wherein the tissue path does not extend to an external incision.

6. The method of claim 1, wherein the extension portion is passed through an external incision.

7. The method of claim 1, wherein an incision is a perirectal incision.

8. A pelvic implant assembly comprising an implant and an insertion tool,
   the implant comprising
      a tissue support portion,
      elongate extension portions extending from the tissue support portion, and
      a dilator located at a distal end of each elongate extension portion, the dilator comprising a curve having a radius of curvature in the range of from 0.5-1.5 centimeters, a sharp tip at a distal end, and an opening at a proximal end, the opening designed and adapted to fit and removably engage a distal end of the insertion tool.

9. The pelvic implant assembly of claim 8, wherein the implant is a mesh strip.

10. The pelvic implant assembly of claim 8, wherein the implant has a length sufficient to extend from a region of an arcus tendineus on a first side of a patient to a region of an arcus tendineus on a second side of the patient.

11. The pelvic implant assembly of claim 8, wherein the tissue support portion has a width greater than a width of the extension portions.

12. The pelvic implant assembly of claim 8, wherein the implant includes a removable sheath that can cover one of the extension portions.

13. The pelvic implant assembly of claim 8, wherein the insertion tool comprises a handle and a longitudinally extending shaft, wherein a proximal end of the extending shaft extends from the handle and a distal end of the extending shaft comprises a radius of curvature.

14. The pelvic implant assembly of claim 13, wherein the dilator has a radius of curvature that matches the radius of curvature of the insertion tool.

15. The pelvic implant assembly of claim 13, wherein the insertion tool is configured to push the dilator through tissue.

16. The pelvic implant assembly of claim 8, wherein the insertion tool comprises a substantially straight shaft.

17. The pelvic implant assembly of claim 8, wherein the insertion tool comprises a curved distal end, the curved portion comprising a radius of curvature in the range of from 0.5-1.5 centimeters.

18. A pelvic implant assembly comprising an implant and a first and second insertion tools,
   the implant comprising
      a tissue support portion,
      a first elongate extension portion extending from an end of the tissue support portion and a second elongate extension portion extending from an opposite end of the tissue support portion, and
      a first dilator located at a distal end of the first extension portion and a second dilator located at a distal end of the second extension portion, each dilator comprising a sharp tip at a distal end and an opening at a proximal end, the opening designed and adapted to engage a distal end of the first and second insertion tools; and
   wherein
      each insertion tool comprises a shaft, a handle, and a curved distal end, the curved distal end comprising a radius of curvature in the range of from 0.5-1.5 centimeters, and the curved distal end being capable of engaging one of the dilators and pushing the dilator through tissue.

19. The pelvic implant assembly of claim 18 comprising a first suture extending along a length of the first extension portion and a second suture extending along a length of the second extension portion.

* * * * *